US012702569B2

(12) United States Patent
Aghazadeh

(10) Patent No.: US 12,702,569 B2
(45) Date of Patent: Aug. 11, 2026

(54) PELVIS REGISTRATION INSTRUMENT AND METHOD

(71) Applicant: ARTHROMEDA, INC., Lowell, MA (US)

(72) Inventor: Mehran S. Aghazadeh, Newton, MA (US)

(73) Assignee: ARTHROMEDA, INC., Lowell, MA (US)

( * ) Notice: Subject to any disclaimer, the term of this patent is extended or adjusted under 35 U.S.C. 154(b) by 41 days.

(21) Appl. No.: 18/389,070

(22) Filed: Nov. 13, 2023

(65) Prior Publication Data

US 2025/0152379 A1 May 15, 2025

(51) Int. Cl.

*A61F 2/46* (2006.01)
*A61B 17/17* (2006.01)
*A61B 34/20* (2016.01)

(52) U.S. Cl.

CPC .......... *A61F 2/4609* (2013.01); *A61B 17/175* (2013.01); *A61B 17/1778* (2016.11); *A61B 34/20* (2016.02); *A61B 17/1746* (2013.01); *A61B 2034/2072* (2016.02); *A61F 2002/4627* (2013.01); *A61F 2002/4633* (2013.01); *A61F 2/4657* (2013.01); *A61F 2002/4658* (2013.01); *A61F 2002/4668* (2013.01)

(58) Field of Classification Search

CPC . A61B 17/175; A61B 17/1778; A61F 2/4657; A61F 2002/4659; A61F 2/4609
USPC .......................................................... 606/91
See application file for complete search history.

(56) References Cited

U.S. PATENT DOCUMENTS 5,540,697 A * 7/1996 Rehmann .............. A61F 2/4609 606/100
8,986,309 B1 3/2015 Murphy
9,138,319 B2 * 9/2015 Fanson .................. A61B 34/25
9,262,802 B2 2/2016 Aghazadeh
9,375,178 B2 6/2016 Aghazadeh
(Continued)

FOREIGN PATENT DOCUMENTS

CN 102740790 A 10/2012
CN 103732165 A 4/2014
(Continued)

OTHER PUBLICATIONS

International Application No. PCT/US2024/055426, International Search Report and Written Opinion, mailed Feb. 11, 2025.

*Primary Examiner* — Matthew J Lawson
(74) *Attorney, Agent, or Firm* — MARSHALL, GERSTEIN & BORUN LLP

(57) ABSTRACT

A pelvis registration apparatus includes a body extending along a longitudinal axis and an engagement assembly coupled to a distal end of the body. The engagement assembly includes three or more contact points that are selectively movable radially with respect to the longitudinal axis of the body to position the contact points at a desired distance relative to a centerline of the body and selectively movable about the body to position the contact points at desired circumferential locations. The pelvis registration apparatus can be provided in a system that further includes position sensors and a controller, where the controller is configured to receive position and orientation data from the position sensors and calculate angular relationships derived from the position and orientation data.

21 Claims, 13 Drawing Sheets

(56) References Cited

U.S. PATENT DOCUMENTS 9,504,482 B2 * 11/2016 Smith ................ A61B 17/1684
9,572,682 B2 2/2017 Aghazadeh
2005/0148843 A1 7/2005 Roose
2005/0251026 A1 * 11/2005 Stone ..................... A61B 34/20 600/407
2008/0255584 A1 * 10/2008 Beverland ............. A61F 2/4609 703/11
2009/0318931 A1 12/2009 Stone et al.
2010/0016984 A1 1/2010 Trabish
2011/0313424 A1 12/2011 Bono et al.
2012/0041445 A1 2/2012 Roose et al.
2012/0157887 A1 6/2012 Fanson et al.
2012/0203140 A1 8/2012 Malchau et al.
2012/0245647 A1 9/2012 Kunz et al.
2012/0323247 A1 12/2012 Bettenga
2013/0274633 A1 10/2013 Hladio et al.
2014/0052137 A1 * 2/2014 Gibson .............. G05B 19/4099 606/91
2015/0012001 A1 1/2015 Theiss et al.
2015/0018718 A1 1/2015 Aghazadeh
2015/0038832 A1 2/2015 Bettenga
2015/0182292 A1 7/2015 Hladio et al.
2015/0196307 A1 7/2015 Keefer
2016/0025622 A1 1/2016 Lavchiev et al.
2016/0038242 A1 * 2/2016 Lo Iacono ................ A61F 2/34 606/86 R
2018/0280157 A1 * 10/2018 Schmit ................... A61B 17/92
2019/0380720 A1 12/2019 Wu et al.

FOREIGN PATENT DOCUMENTS

CN 104244860 A 12/2014
JP 2014508549 A 4/2014
WO WO-2010/063117 A1 6/2010
WO WO-2012/173890 A2 12/2012
WO WO-2014/028227 A1 2/2014
WO WO-2015/089118 A1 6/2015

* cited by examiner

PELVIS REGISTRATION INSTRUMENT AND METHOD

FIELD OF THE DISCLOSURE

The present disclosure generally relates to surgical procedures and, more particularly, to systems, devices, and methods utilized in prosthetic implantation surgeries.

BACKGROUND

Successful prosthetic surgery requires precise intra-operative placement and positioning of replacement structures as implants within the patient, such that the in vivo function of the reconstructed joint is optimized biomechanically and biologically. For the surgeon, it is necessary to ensure that the replacement structural components are implanted correctly and function in situ properly in order to avoid intra-operative and post-operative complications, as well as to ensure a long lasting action and use for the implanted prosthesis.

While applicable to any prosthetic implant, one example where placement and positioning are important is hip arthroplasty. In such an operation, a malpositioned hip prosthesis will not adequately restore the joint's biomechanics, will not function properly, and is at increased risk of intra-operative and post-operative complications. Such complications can include, without limitation, dislocation, impingement, fracture, implant failure, aseptic loosening, and subsidence. A malpositioned prosthetic implant is particularly susceptible to dislocation and early loosening because the prosthesis will not be well fitted or supported within the host's native bone.

One problem routinely faced by surgeons in hip arthroplasty procedures is how to achieve proper acetabular prosthetic implant alignment. It is generally agreed among orthopedic surgeons that the ideal anatomic position (for most patients) for an acetabular prosthetic implant within the native bone of the host's hip is at 45° (degrees) of inclination. Despite this general agreement, however, surgeons often select different desired angles of inclination based on the particular anatomy and native positions and motions of a given patient.

A second important angle is the angle of anteversion. The range of optimum angles of anteversion can vary widely based on a patient's anatomy, biomechanics, and flexibility of different joints, among other factors. As a result and similar to inclination as described above, surgeons often select different angles of anteversion for different patients. More recent techniques emphasize "combined anteversion" of a reconstructed hip, rather than a prosthetic cup's absolute angle of anteversion. Combined anteversion is the sum of the angle of anteversion of the cup and the angle of anteversion of a stem that is fitted into a patient's femur. Since there is limited space for changing the stem's angle of anteversion, adjusting the position of the cup to that of the stem is critical to improving stability of the reconstructed hip and reducing impingement.

Precise measurement of these specific angles, and therefore proper placement of the prosthesis, has been difficult to achieve, mostly because these angles are relative to the patient's pelvis and it is not possible to precisely identify spatial position of the pelvis. Additionally, the patient is covered by sterile surgical drapes during the course of a hip replacement operation. It is difficult to monitor any change in position of the patient's pelvis that can occur after draping the patient for the surgery, including, for example, any change in position that may occur during the operation.

Prior techniques for addressing these issues have included the use of electronic position sensors, e.g., one coupled to a patient's pelvis and the other to an instrument used to position a prosthesis, to monitor positioning of the patient relative to the instrument and prosthesis coupled thereto. In order to accurately determine the critical reference angles mentioned above, however, the electronic position sensor coupled to the pelvis has to be aligned with anatomical planes of the patient's body in a known manner. To accomplish this, a guide is required to orient the electronic position sensor prior to attachment to the patient's pelvis. The time required to properly prepare such a guide can increase the overall time and cost associated with the operation. Also, not being reusable will place possibility and integrity of the surgical procedure at some level of risk.

A recent development in the orthopedics field is the use of patient-specific components during surgical procedures. Such components can include a prosthesis itself or a guide for placing another component, making a cut in tissue or bone, etc. Patient-specific components can be created prior to an operation from a 3-dimensional model of a patient's anatomy and can be configured to interface with the patient's acetabulum in only one orientation. While such a component can therefore be less prone to user error, as it fits against or into a patient's body in only one correct manner, it can be costly and time consuming to produce a guide for each patient, either by 3-D printing or other means.

SUMMARY

There is a need for pelvis registration instruments, systems, and methods to improve prosthesis positioning and streamline surgical procedures while maximizing accuracy and ease of use.

In accordance with a first aspect, a pelvis registration apparatus is disclosed herein that includes a body extending along a longitudinal axis and having a distal end and a proximal end, and an engagement assembly coupled to the distal end of the body. The engagement assembly includes three or more contact points that are: selectively movable radially with respect to the longitudinal axis to position the feet at a desired radius relative to a centerline of the body, and selectively movable about the body to position the feet at desired circumferential locations. The pelvis registration apparatus can include one or more lock mechanisms to restrict movement of the contact points after the initial patient-specific adjustment to ensure accuracy and ease of use.

In some examples, the engagement assembly can include three or more leg linkages coupled to the body, where each leg linkage provides one or more of the contact points. The leg linkages can each include a leg member having a proximal end and an opposite, distal end, where the proximal ends of the leg members are pivotably coupled to the body about a pivot axis perpendicular to the longitudinal axis to position the distal ends of the leg members at the desired radius. The leg linkages can further be rotatable about the body to selectively position the leg assemblies at desired circumferential locations.

In some examples, the contact point can be a foot pivotably coupled to the distal end of the leg member; and/or each leg linkage can include a support member having a proximal end pivotably coupled to the body and a distal end pivotably coupled to an intermediate portion of the leg member.

In some examples, the body can include an outer shaft and an inner shaft extending within the outer shaft, where the proximal ends of the support member are coupled to the inner shaft. The apparatus can further include a handle coupled to the inner shaft and threadingly engaged with the outer shaft, such that rotation of the handle causes the inner shaft to move longitudinally with respect to the outer shaft, movement of the inner shaft causing the support member to move the distal ends of the leg members radially with respect to the body.

In further examples, the outer shaft can include sizing gradation indications thereon for adjusting the instrument based on a patient specific value; and/or the apparatus can include a radial lock collar arranged around the body, where the annular lock is slidable with respect to the handle along the longitudinal axis and biased to a locked position preventing rotation of the handle relative to the outer shaft.

In some examples, each leg linkage further can include a top mount including a bracket having the proximal end of the leg member pivotably mounted thereto and a guide disc extending radially inward from the bracket, where the guide disc is arranged around the body and fixed with respect to the outer shaft, and a bottom mount including a bracket having the proximal end of the support member pivotably mounted thereto and a follower disc extending radially inward from the bracket, where the follower disc extends around the body and is fixed with respect to the outer shaft.

In further examples, the guide discs and the follower discs of the leg linkages can be disposed in a stacked relation to one another along the body; the bracket of the top mount can include one or more grip recesses for aiding in circumferential leg assembly adjustment; and/or the body can include an extension tip extending distally from the outer shaft around the inner shaft and fixed with respect to the outer shaft, where the guide discs of the leg assemblies are disposed around the extension tip.

In some examples, the apparatus can include a slider mounted to the extension tip distally of the guide discs, where the slider is configured to engage the brackets of the top mounts to prevent unwanted circumferential movement thereof; the apparatus can include a circumferential lock collar arranged around the extension tip and longitudinally movable with respect thereto, where the circumferential lock collar is slidable with respect to the extension tip along the longitudinal axis and biased to a locked position engaging the top mounts of the leg assemblies and preventing circumferential movement of the leg assemblies relative to the extension tip.

In further examples, the circumferential lock collar can include an outwardly extending ring portion, where the ring portion is configured to provide a stop surface for the circumferential lock collar when manipulated away from the locked position to allow circumferential movement of the leg assemblies; and/or the extension tip can include angular gradation indications therearound and each top mount of the leg assemblies can include a pointer shiftable along the angular gradation indications when the leg assemblies are manipulated around the body to indicate a circumferential location for each of the contact points.

In any of the above examples, the apparatus can include one or more of the following aspects: the apparatus can include a sensor mount coupled to the body, where the sensor mount is configured to have a sensor removably coupled thereto; at least one of the body or engagement assembly can include openings extending therethrough to provide access to interior surfaces thereof for cleaning; or the apparatus can include acetabulum data from one or more computed tomography scans of a patient, where the desired sizing and desired circumferential locations for the feet of the engagement assembly are determined based on the acetabulum data.

In accordance with a second aspect, any of the above examples can be provided in a system for use in implanting a prosthesis that further includes a controller and first and second position sensors capable of reporting position and orientation data to the controller. The first position sensor is removably coupled to the pelvis registration apparatus and the second position sensor is disposed in a fixed, spaced relation relative to the first electronic position sensor. The controller is configured to: receive the position and orientation data from the first and second position sensors and calculate angular relationships derived from the position and orientation data. In further forms, the second electronic position sensor can be configured to be coupled to a patient's bony anatomic structure, e.g., the pelvis.

The system can further include one or more of the following aspects: the angular relationships can include one or more of angle of inclination and angle of anteversion; the controller can be configured to calculate the angular relationships on demand; or the controller can be configured to calculate the angular relationships continuously in real time.

In accordance with a third aspect, a method for prosthesis implantation is disclosed that includes analyzing acetabulum data of a patient to: determine a geometry of an acetabular rim of the patient and identify three or more unique locations along the acetabular rim. The method further includes manipulating an engagement assembly of a pelvis registration apparatus to: position three or more contact points of the engagement assembly at a radius relative to a centerline of a body of the pelvis registration apparatus corresponding to geometry of the acetabular rim and position the three or more contact points at circumferential locations corresponding to the three or more unique locations.

In some examples, manipulating the engagement assembly to position the three or more contact points at the radius relative to the center of the body can include rotating a handle of the pelvis registration apparatus to move an inner shaft of the body along a longitudinal axis of the body relative to an outer shaft of the body, movement of the inner shaft causing leg members of the engagement assembly to pivot about pivot axes perpendicular to the longitudinal axis of the body, the contact points comprising feet coupled to distal ends of the leg members. In further examples, the method can include manipulating a radial lock collar arranged around the body to disengage the radial lock collar from the handle, allowing the handle to be rotated.

In some examples, manipulating the engagement assembly to position the three or more contact points at the circumferential locations can include moving leg linkages around a perimeter of the body. In further examples, the method can include manipulating a circumferential lock collar arranged around the body to disengage the circumferential lock collar from the leg linkages, allowing the leg linkages to be moved around the perimeter of the body.

In some examples, the method can include positioning the pelvis registration apparatus against the acetabular rim of the patient, such that the three or more contact points engage the three or more unique locations along the circumference of the acetabular rim, coupling a first position sensor to the pelvis registration apparatus, and coupling a second position sensor to a bony anatomic structure of a patient.

In further examples, the method can include removing the pelvis registration apparatus, coupling the first position sensor to an instrument that is coupled to a prosthesis, receiving position and orientation data from the first and second position sensors at a controller, calculating angular relationships derived from the position and orientation data, and displaying the angular relationships of the prosthesis relative to the bony anatomic structure.

In further examples, the method can include receiving alignment position and orientation data from the first and second position sensors at the controller with the first position sensor coupled to the pelvis registration apparatus and providing guidance to a user to move the instrument with the first position sensor coupled thereto such that the position and orientation data from the first and second position sensors matches the alignment position and orientation data.

DETAILED DESCRIPTION

Figure 1:
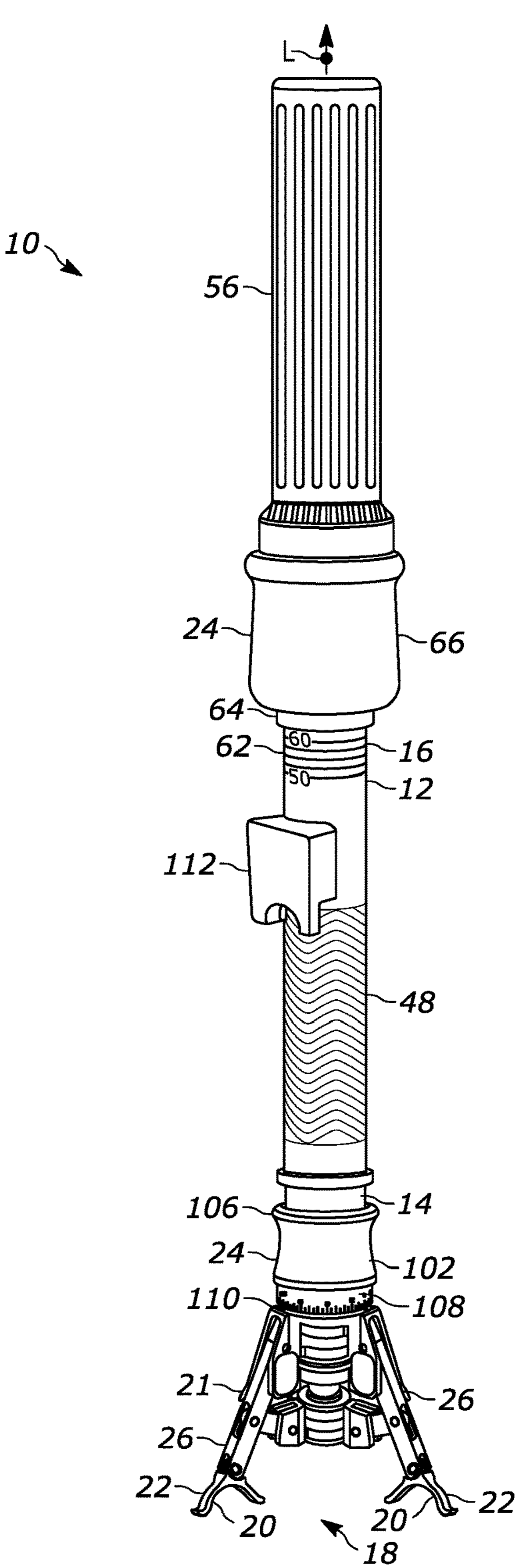
FIG. 1 is a perspective view of a pelvis registration instrument in accordance with various examples of the application.

Systems and methods are described herein that provide patient-specific configurations using a pelvis registration instrument for hip arthroplasty procedures. The disclosed instruments and systems provide valuable advantages relative to prior techniques, including increased ease of use, reduced time required for the preparation of the procedure, reduced procedure complexity, and reduced procedure cost.

The systems and methods described herein can make use of one or more position sensors and a patient-specific pelvis registration instrument to accurately and quickly position a prosthesis during, for example, a hip arthroplasty procedure. The systems and methods described herein can utilize an pelvis registration instrument to provide registration relative to anatomical planes of the patient's body. As described in more detail below, the pelvis registration instrument can have a patient-specific engagement assembly configuration set prior to a surgical procedure to reduce time required in an operating room. Moreover, possible errors that might occur due to a surgeon or other user incorrectly positioning an electronic sensor can be reduced or eliminated.

The pelvis registration instrument includes an engagement assembly with three or more patient contact points that are both movable radially and outwardly to be set at a radius corresponding to the anatomy of a particular patient's acetabular rim and movable circumferentially to be set at points corresponding to unique locations along the patient's acetabular rim. A physician can analyze the patient's scan data to determine the acetabular rim diameter, as well as identify the unique locations on the patient's acetabular rim. This configuration ensures that the pelvis registration instrument seats anatomically in a specific position and orientation with regard to the patient's acetabulum and anatomic planes, thereby ensuring that sensor data subsequently collected utilizing the pelvis registration instrument correctly maps a patient's pelvis relational spatial position angles. This sensor data can then be utilized to guide the placement of a hip prosthesis to a desired angle of inclination and forward flexion relative to the patient's pelvis.

Details of example pelvis registration instruments 10 are shown in FIGS. 1-6. The instrument 10 includes an elongate body 12 extending along a longitudinal axis L, and having a distal end 14 and an opposite, proximal end 16. An engagement assembly 18 of the instrument 10 is coupled to the distal end 14 of the body 12 and includes three patient contact points 20. Although the instrument 10 is shown with three patient contact points 20, it will be understood that the instrument 10 could alternatively include four, five, or more contact points 20 having similar configurations to those described herein. The contact points 20 are selectively movable radially with respect to the longitudinal axis L of the body 12 so that the contact points 20 can be positioned at a desired radius relative to a centerline of the body 12. Further, the contact points 20 are selectively movable about the body 12 so that the contact points 20 can be positioned at desired circumferential locations relative to one another around the body 12. In one example, the contact points 20 can be feet 22. Further, as described in more detail below, the instrument 10 can also include one or more lock mechanisms 24 that restrict movement of the contact points 20 in the radial and/or circumferential directions.

As shown, the engagement assembly 18 can include three leg linkages 26 that are coupled to the body 12 at the distal end 14 thereof. In this example, ends of the leg linkages 26 provide the patient contact points 20 described above. Pursuant to this, each of the leg linkages 26 are independently rotatable about the body 12 as described above, so that the contact points 20 can be selectively positioned at desired circumferential locations.

Each of the leg linkages 26 includes a main leg member 28 having a distal end 30 and an opposite, proximal end 32. In some examples, distal end 30 of the leg member 28 can provide the patient contact point 20. In other examples, the leg linkages 26 can further include feet 22 pivotably coupled to the distal ends 30 of the leg members 28 to provide the patient contact points 20. If desired, the feet 22 can have an arched configuration with a concave inner surface as shown to better engage/grip the acetabular rim 232 (FIG. 11) of a patient.

To provide radial movement functionality, the proximal ends 32 of the leg members 28 are pivotably coupled to the body 12 about a pivot axis P1 that extends perpendicular to the longitudinal axis L of the body 12. This configuration allows the distal ends 30 of the leg members 28, and the feet 22 coupled thereto, to be moved, e.g., pivoted inwardly and outwardly, to dispose the contact points 20 at a desired radius relative to a centerline of the body 12.

The leg linkages 26 each further include a support member 34 with a distal end 36 pivotably coupled to an intermediate portion 38 of the leg member 28, e.g., between the distal and proximal ends 30, 32 thereof, about a pivot axis P2 that extends perpendicular to the longitudinal axis L of the body 12 and a proximal end 40 pivotably coupled to the body 12 about a pivot axis P3 that extends perpendicular to the longitudinal axis L of the body 12.

As shown, the pivot connections for the leg member 28 with the support member 34 and the leg member 28 with the foot 22 can have an internal configuration with the leg member 28 having through openings/cavities 42 to receive the distal end 36 of the support member 34 and a proximal end 44 of the foot 22 therein. Thereafter, a pin 46 can be inserted through the leg member 28 and support member 34/foot 22 to provide the pivot axes P1, P2 thereof.

Figure 3:
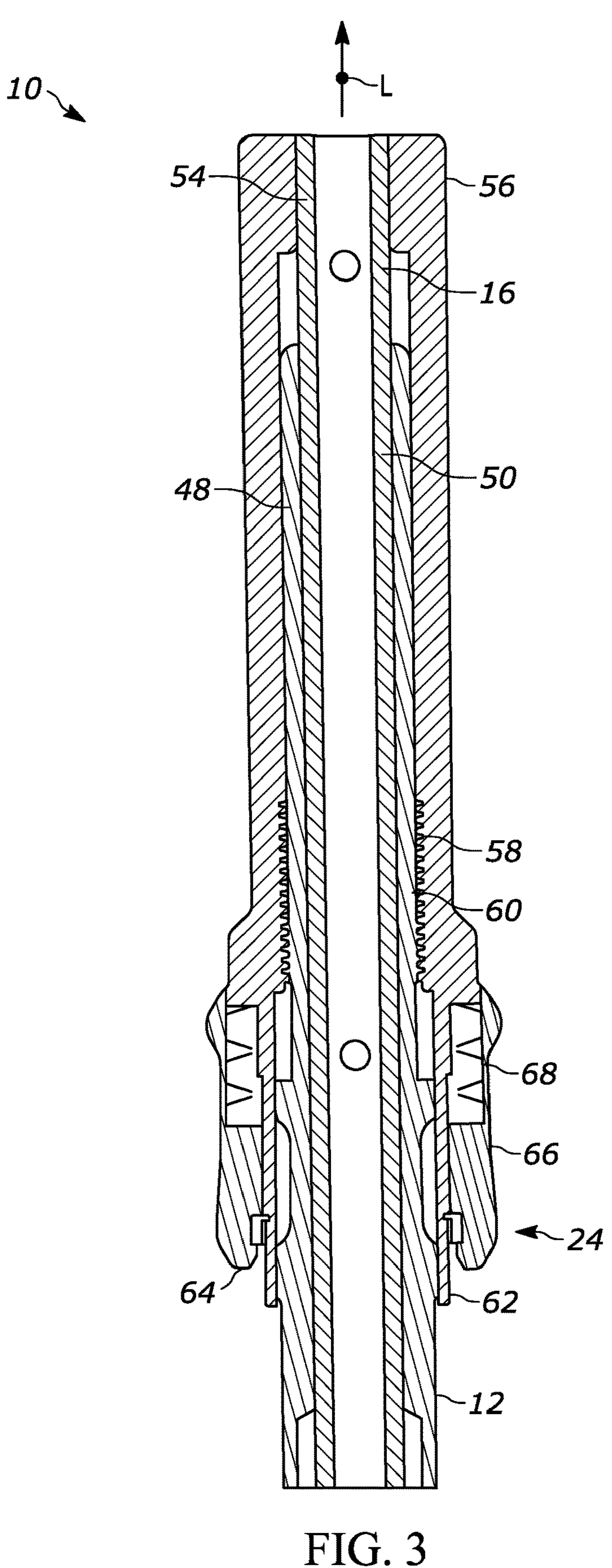
FIG. 3 is a cross-sectional view of a proximal end of the pelvis registration instrument of FIG. 1.
Figure 4:
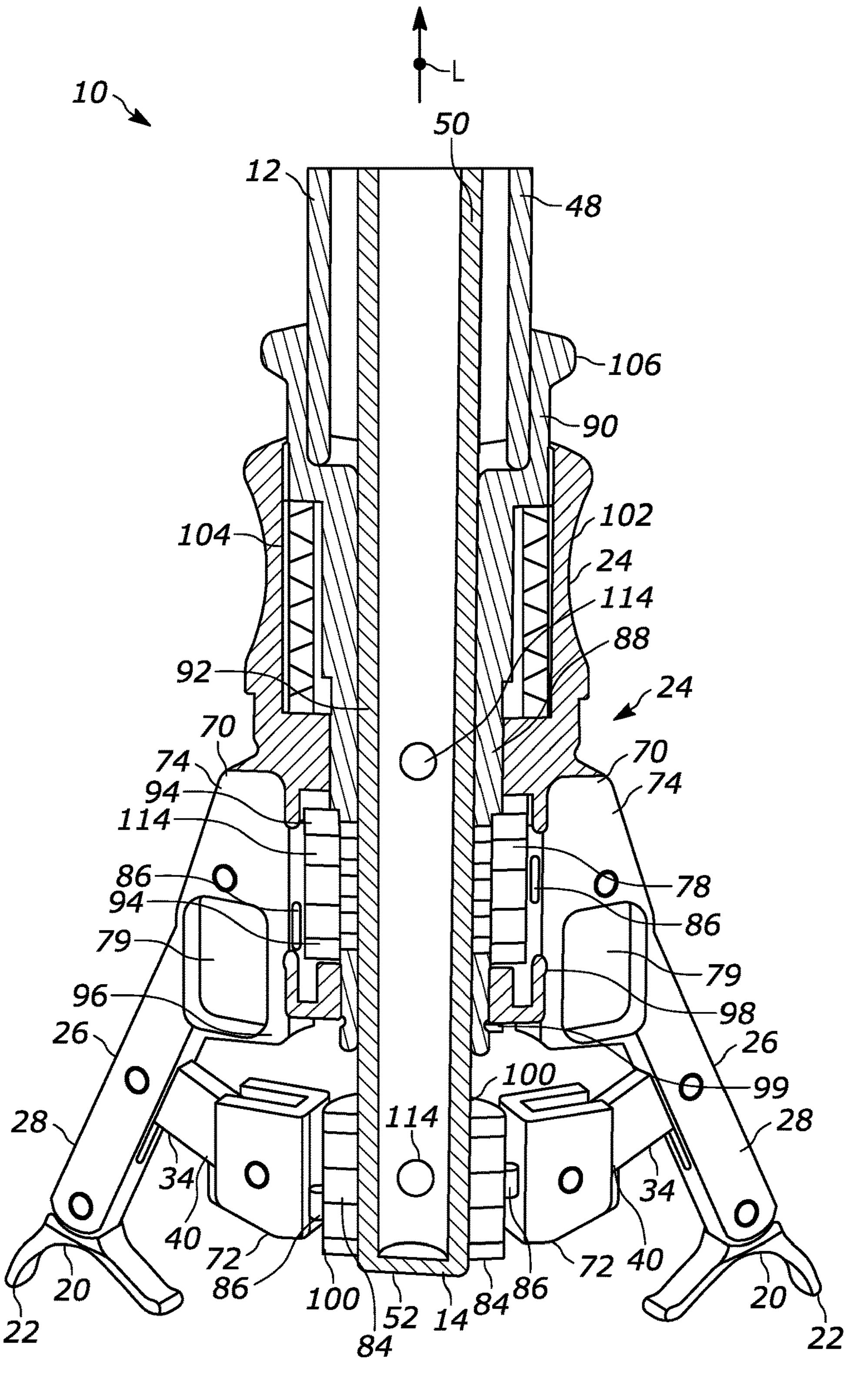
FIG. 4 is a cross-sectional view of a distal end of the pelvis registration instrument of FIG. 1 showing circumferential adjustment features and an engagement assembly.

Further details of the body 12 and the engagement assembly 18 are shown in FIGS. 3 and 4. For example, the body 12 can include an outer shaft 48 and an inner shaft 50 telescopingly received within the outer shaft 48. As shown, distal and proximal ends 52, 54 of the inner shaft 50 extend below and above the outer shaft 48, respectively, to engage other components of the instrument 10. For example, the proximal ends 40 of the support members 34 are coupled to the distal end 52 of the inner shaft 50 and a handle 56 is coupled to the proximal end 54 of the inner shaft 50. As shown in FIG. 3, the handle 56 includes an internal thread 58 configured to engage an external thread 60 on the outer shaft 48, such that the handle 56 can be rotated to move upward and downward on the outer shaft 48. This functions to drive upward and downward longitudinal movement of the inner shaft 50 relative to the outer shaft 48 due to the handle 56 coupling to the inner shaft 50. Further, because the support members 34 of the leg linkages 26 are coupled to the inner shaft 50, movement of the inner shaft 50 causes the support member 34 to move the distal ends 30 of the leg members 28 radially with respect to the body 12. More specifically, the proximal ends 32 of the leg members 28 are stationary with respect the outer shaft 48 of the body 12, so that the relative movement of the outer and inner shafts 48, 50 causes the proximal ends 32, 40 of the leg members 28 and the support members 34 to move relative to one another. With the configuration shown, clockwise rotation of the handle 56 causes the inner shaft 50 and proximal ends 40 of the support members 34 to move downwardly, pulling the intermediate portions 38 of the leg members 28 inwardly to thereby decrease a radial position of the contact points 20. Further, with this configuration, each of the contact points 20 are disposed at a same radius away from a centerline of the body 12.

If desired, to provide feedback and easy functionality for a user, the outer shaft 48 can include sizing gradation indications 62 adjacent to a distal end surface 64 of the handle 56 as shown in FIG. 1. The indications 62 and handle end surface 64, along with the dimensions of the body 12 and leg linkages 26, can be configured, such that the handle end surface 64 aligns with individual values of the sizing gradation indications 62 corresponding to patient-specific locations of on which the contact points 20 of the engagement assembly 18 are currently disposed. Stated another way, the handle distal end surface 64 can be utilized to indicate a size (e.g., dimension) on which the feet 22 of the leg linkages 26 are disposed and allow easy adjustment. This allows a user to easily set the engagement assembly 18 at a calculated size (e.g., a calculated diameter) for a patient as indicated by scan data, as explained in more detail below.

Figure 2:
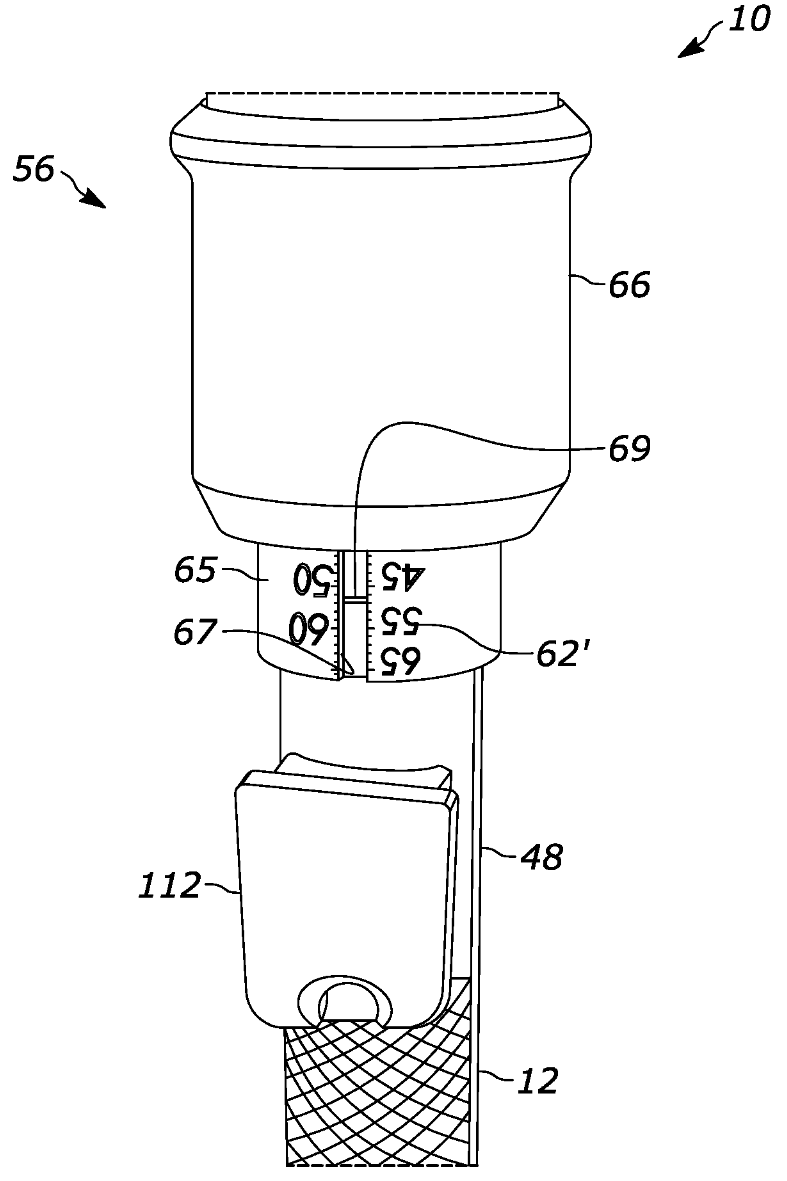
FIG. 2 is a sectional perspective view of an alternative proximal end of the pelvis registration instrument of FIG. 1.

Another example for providing sizing gradation indications 62' is shown in FIG. 2. In this example, the indications 62' are included on a distal collar 65 of the handle 56 adjacent to a longitudinal slot 67 defined by the collar 65. The outer shaft 48 includes a circumferential line 69 that is visible through the slot 67. With this configuration, the indications 62' and the circumferential line 69, along with the dimensions of the body 12 and leg linkages 26, can be configured, such that the circumferential line 69 aligns with individual values of the sizing gradation indications 62' corresponding to a dimension on which the contact points 20 of the engagement assembly 18 are currently disposed. This allows a user to easily set the engagement assembly 18 at a calculated size (e.g., a calculated diameter) for a patient as indicated by scan data, as explained in more detail below As briefly discussed above, the instrument 10 can include one or more locking mechanisms 24 configured to selectively restrict movement of the contact points 20. To restrict inward and outward radial movement of the contact points 20, the instrument 10 can include an annular radial lock collar 66 extending around the handle 56 and biased to a locked position by a spring 68 captured between surfaces of the handle 56 and the lock collar 66. In the locked position, the lock collar 66 prevents relative rotation of the handle 56 and the outer shaft 48. To allow the handle 56 to be rotated relative to the outer shaft 48, a user can slide the lock collar 66 rearwardly against the force of the spring 68 along the handle 56 to a use position which disengages the lock collar 66 from the handle 56. If desired, an outer surface of the lock collar 66 can have a contoured configuration with a rear lip, which provides an ergonomic grip for the user.

To aid in gripping the instrument 10, an outer surface of the outer shaft 48 can have a knurled or otherwise textured configuration or coating. Additionally, the handle 56 can have a fluted configuration with a plurality of longitudinally extending ribs. Other textured configurations or coatings can alternatively be utilized.

Figure 5:
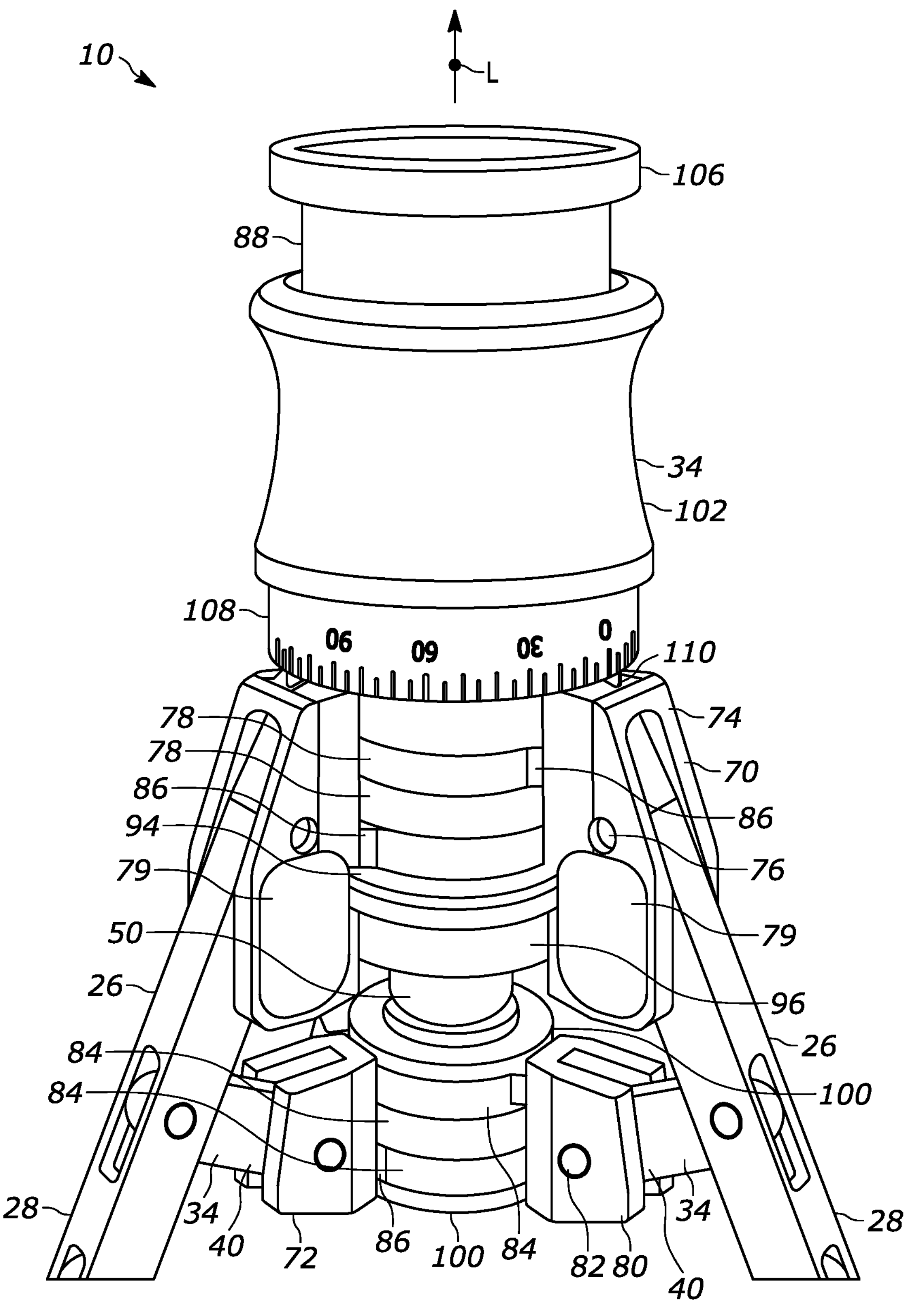
FIG. 5 is a sectional perspective view of the distal end of the pelvis registration instrument of FIG. 1.

Details of the circumferential movement functionality are shown in FIGS. 4 and 5. More specifically, in one example, the leg linkages 26 can be rotatably mounted to the body 12 so that the contact points 20 can be disposed in the desired circumferential locations. Pursuant to this, the leg linkages 26 can include a top mount 70 for the leg member 28 and a bottom mount 72 for the support member 34. As best shown in FIG. 5, each of the top mounts 70 includes an outer bracket 74 that pivotably receives the proximal end 32 of the leg member 28 therein. The leg member 28 is pivotably mounted to the bracket 74 by a pin 76 or other suitable pivot connection. The top mount 70 further includes an annular guide disc 78 that extends radially inward from the bracket 74 to be concentrically arranged around the body 12. The top mount 70, and therefore the leg member proximal end 32, is longitudinally fixed with respect to the outer shaft 48. If desired, the bracket 74 can have an extended configuration with one or more grip recesses 79 defined in sides thereof for aiding in circumferential leg assembly adjustment.

Each of the bottom mounts 72 includes an outer bracket 80 that pivotably receives the proximal end 40 of the support member 34 therein. The support member 34 is pivotably mounted to the bracket 80 by a pin 82 or other suitable pivot connection. The bottom mount 72 further includes an annular follower disc 84 that extends radially inward from the bracket 80 to be arranged around the body 12. The bottom mount 72, and therefore the support member proximal end 40, is longitudinally fixed with respect to the inner shaft 50. The guide and follower discs 78, 84 are disposed in a stacked relation to one another along a length of the body 12. To accommodate this configuration, the guide and follower discs 78, 84 connect to their respective mount 70, 72 at three different longitudinal locations by radial connections 86.

As shown in FIG. 4, the body 12 can further include an extension tip 88 that is coupled to a distal end of the outer shaft 50 and fixed longitudinally with respect thereto. The extension tip 88 can have a nozzle configuration with a mount portion 90 disposed over the distal end of the outer shaft 50 and a reduced diameter distal portion 92 extending away from the mount portion 90. The distal portion 92 is disposed around the inner shaft 52 and configured so that the inner shaft 52 is longitudinally moveable with respect thereto. The three stacked guide discs 78 are rotatably coupled to and arranged concentrically around the distal portion 92 of the extension tip 88. The guide discs 78 can be held in place on the extension tip 88 by top and bottom washers 94 longitudinally fixed on the extension tip 88. In one example, the instrument 10 can also include an annular slider 96 mounted to the inner shaft 52 distal of the stacked guide discs 78. The slider 96 engages an inner surface of the top mount bracket 74 to prevent unwanted circumferential movement of the leg assemblies 26. For example, as shown in FIG. 4, the slider 96 can include a radial protrusion that fits within a radial groove 98 defined in the top mount bracket 74 inner surface. In one example, the extension tip 88 can include annular walls 99 extending therearound defining a channel to receive the guide discs 78 and washers 94 and a channel to receive the slider 96. The three stacked follower discs 84 are arranged concentrically around the distal end 52 of the inner shaft 50. Similar to the above, the follower discs 84 can be held in place on the inner shaft 50 by top and bottom washers 100 longitudinally fixed on the inner shaft 50.

As briefly discussed above, the instrument 10 can include one or more locking mechanisms 24 configured to selectively restrict movement of the contact points 20. To restrict rotational/circumferential movement of the contact points 20, the instrument 10 can include an annular positional adjustment collar 102 extending around the extension tip 88 and biased to a locked position by a spring 104 captured between surfaces of the extension tip 88 and the lock collar 102. In the locked position, the lock collar 102 engages the top mounts 70 of the leg assemblies 26 to prevent circumferential movement of the leg assemblies 26 relative to the body 12. To allow the leg assemblies 26 to be circumferentially moved around the body 12, a user can slide the lock collar 102 rearwardly against the force of the spring 104 along the extension tip 88 to a use position, which disengages the lock collar 102 from the top mounts 70, allowing the leg assemblies 26 to be freely moved circumferentially around the body 12. If desired, the mount portion 90 of the extension tip 88 can include a radially protruding ring 106 configured to act as a stop surface for the lock collar 102 when shifted away from the lock position to hold the lock collar 102 in the use position. Further, an outer surface of the lock collar 102 can have a contoured configuration with a rear lip, which allows a user to both hold the lock collar 102 in the use position with one hand, freeing the other hand to move the leg assemblies 26.

In one example, to provide feedback and easy functionality for a user, the lock collar 102 can include angular gradation indications 108 disposed along an edge thereof adjacent to a top of the top mounts 70, as shown in FIG. 5. The indications 108 can include sequential markings between 0 and 360 or ratios thereof, such as 0-60, 0-120, 0-180, etc. Using these indications 108, a user can align each of the top mounts 70 at a desired circumferential location. This allows a user to easily set the leg assemblies 26 at circumferential locations corresponding to the unique locations of the patient's acetabular rim identified in patient data, as explained in more detail below. To provide better accuracy, the top mounts 70 can each include a pointer 110 that extends proximally along the body 12 to be radially outward of the indications 108, allowing a user to shift the top mounts 70 around the lock collar 102 to align the point 110 with a desired marking of the indications 108. This provides a clear indication to the user of circumferential locations for each of the contact points 20 relative to one another. In one implementation, the pointer 110 can engage the lock collar 102 to be utilized as a part of the locking mechanism 24.

Figure 6:
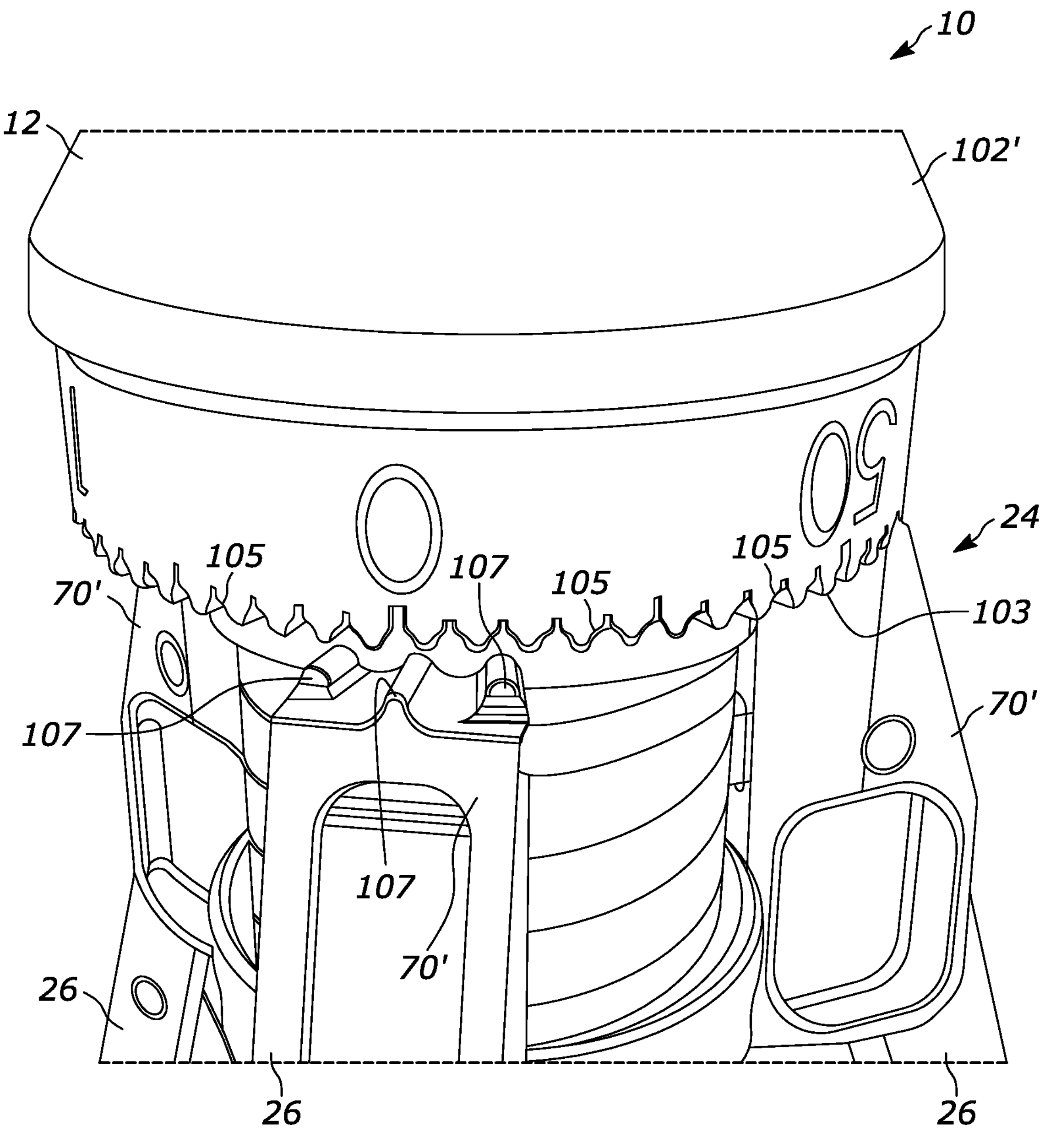
FIG. 6 is a sectional perspective view of an alternative distal end of the pelvis registration instrument of FIG. 1.

Another example locking mechanism 24 configured to restrict rotational/circumferential movement of the contact points 20 is shown in FIG. 6. In this form, the instrument 10 can include an annular positional adjustment collar 102' extending around the extension tip and biased to a locked position by a spring (not shown). The collar 102' includes a serrated lower edge 103 having spaced recesses 105. Further, the top mounts 70' of this form include one, two, or three as shown upwardly extending protrusions 107 sized to fit within the recesses 105 of the collar 102'. In the locked position, the lock collar 102 engages the top mounts 70' of the leg assemblies 26 such that the protrusions 107 are received within the recesses 105, which prevents circumferential movement of the leg assemblies 26 relative to the body 12. To allow the leg assemblies 26 to be circumferentially moved around the body 12, a user can slide the lock collar 102' rearwardly against the force of the spring along the extension tip to a use position, which disengages the lock collar 102' from the top mounts 70', allowing the leg assemblies 26 to be freely moved circumferentially around the body 12. As with the above form, an outer surface of the lock collar 102' can have a contoured configuration with a rear lip, which allows a user to both hold the lock collar 102' in the use position with one hand, freeing the other hand to move the leg assemblies 26.

In one example, to provide feedback and easy functionality for a user, the lock collar 102' can include angular gradation indications 108' disposed along an edge thereof adjacent to a top of the top mounts 70', as shown in FIG. 6. The indications 108' can include sequential markings between 0 and 60 or other ranges, such as 0-120, 0-180, 0-360, etc. Using these indications 108', a user can align each of the top mounts 70' at a desired circumferential location. This allows a user to easily set the leg assemblies 26 at circumferential locations corresponding to the unique locations of the patient's acetabular rim identified in patient data, as explained in more detail below. To provide better accuracy, one of the protrusions 106 can be disposed in a middle of the top mounts 70', allowing a user to shift the top mounts 70' around the lock collar 102' to align the middle protrusion 106 with a desired marking of the indications 108'. This provides a clear indication to the user of circumferential locations for each of the contact points 20 relative to one another.

As shown in FIG. 1, the instrument 10 can further include a sensor mount 112 coupled to the body 12, such as the outer shaft 48 thereof, to provide a secure coupling location for a position sensor, as described in more detail below.

In some examples, the instrument 10 can include one or more openings 114 that extend through components thereof to provide access to interior surfaces of the instrument 10 cleaning and sterilization between uses. For example, the extension tip 88 and/or the inner shaft 50 can include openings 114 disposed radially and/or axially there along.

As discussed above, a physician can utilize patient scan data to determine the radial and circumferential locations for the contact points 20 prior to a surgery. The scan data can be acetabulum data compiled from one or more computed tomography scans of a patient.

Figure 7:
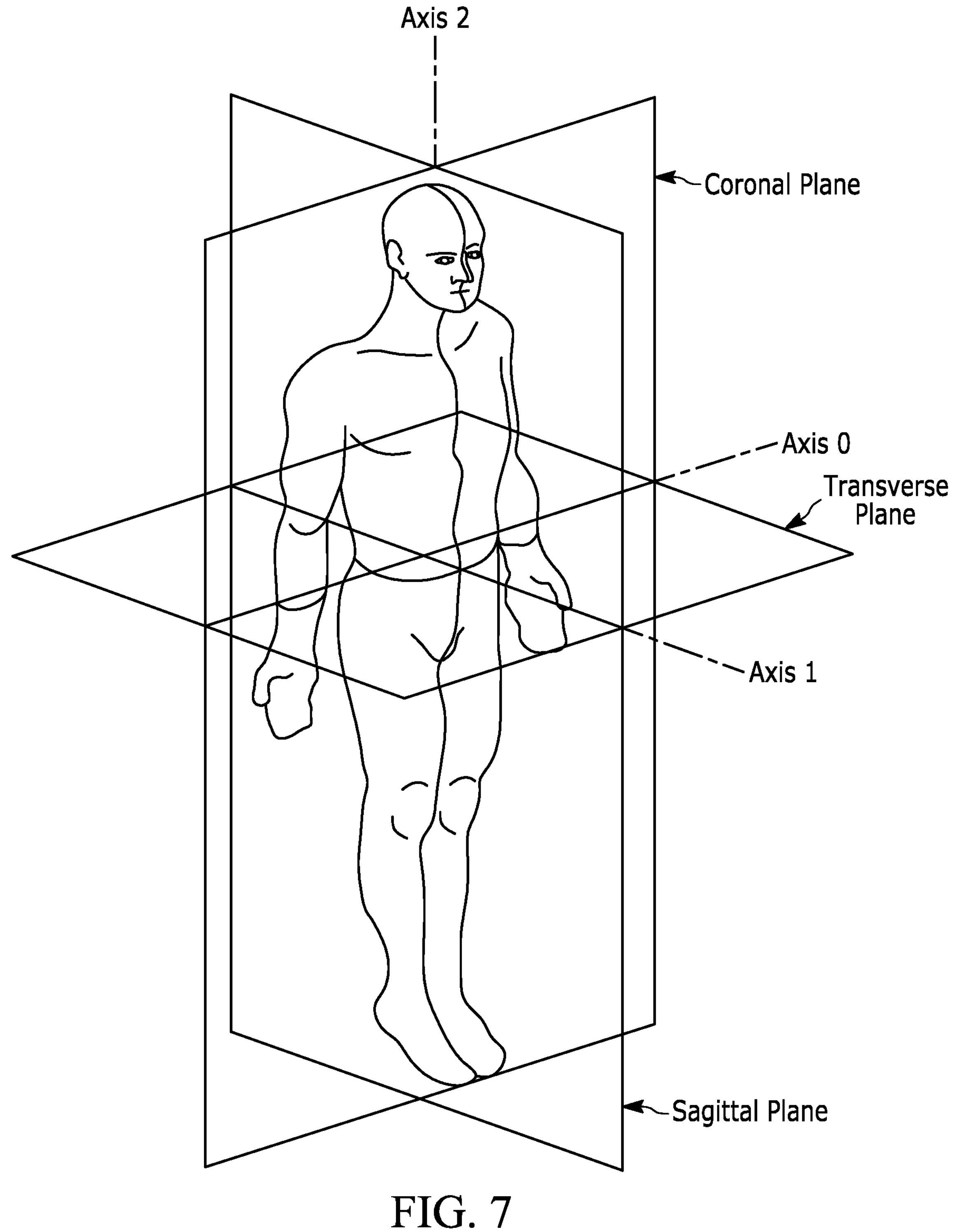
FIG. 7 illustrates various anatomical planes and axes of the human body.

Before discussing details of a system utilizing the pelvis registration instrument 10 discussed above, it will be helpful to discuss background information regarding the anatomical planes of the human body, as well as patient orientation information for hip arthroplasty surgical procedures. As shown in FIG. 7, the transverse or axial plane divides the human body into top and bottom sections, the coronal plane divides the body into front (anterior) and back (posterior) portions, and the sagittal plane divides the body into left-sided and right-sided portions. Also, by definition anterior pelvis plane is defined by four most anterior body land mark over each ASIS (Anterior Superior Iliac Spine) and pubic tubercle on right and right side of pelvis.

A human patient having hip joint replacement surgery is traditionally placed in the lateral decubitus position, i.e., lying down on the side opposite the surgical side. In this position, the patient's operative hip is up. Alternatively, a patient having hip joint replacement surgery can be placed in the supine position, i.e., lying on the back. Other patient positions are possible, for example, when undergoing procedures to replace other joints (e.g., knee, etc.).

The following term definitions are also employed routinely herein. When discussing hip replacement surgery, angle of inclination is the angle between the axis of the acetabulum or acetabular implant and the sagittal plane. Angle of anteversion is the angle between the axis of the acetabulum or acetabular implant and the anterior pelvis plane. The angle of femoral neck anteversion is the angle between the axis of the femoral neck and the epicondylar axis (of the distal femur). Epicondylar axis is a line connecting medial and lateral epicondyles of the distal femur.

As shown in FIGS. 8-14, with reference to a hip replacement procedure, a system as provided herein utilizes a plurality of sensors and specially designed software executable on a computing device together to electronically measure or calculate: (1) the bony pelvis' position while lying on the operating table during surgery by coupling one of the electronic position sensors to the pelvis such that it can track movements thereof; and (2) the angles of inclination and anteversion of the native acetabulum before and while being prepared, as well as the acetabular prosthesis while being implanted into the native bone. Advantageously, the need to position the sensor coupled to the pelvis in any particular manner relative to anatomical planes of the patient's body can be eliminated by use of the pelvis registration instrument 10 described above because, as is explained in more detail below, the orientation of the instrument relative to the anatomical planes is known when the contact points 20 are positioned against the identified unique locations of the patient's anatomy to which it was configured to engage. The measurements of the system can be made electronically and, if desired, continuously. The measurements can be calculated in real time and in true relationship to the pelvis reference planes during preparation of the bone and while the prosthesis is being surgically implanted into the native bone structure.

The methodology and system described herein can provide an intra-operative surgical positioning assessment and angle determination made by referencing an orientation (that has a known relation to a patient's anatomical planes) provided by the pelvis registration instrument 10 discussed above. The method and system provide precise information about the angles of inclination and anteversion of the native bony acetabulum and prosthesis for proper implantation. These measurements and calculations can be made in true relationship to the pelvis reference planes during the time when the surgeon is preparing the bone and handling the prosthesis and is inserting it into the native bone structure.

Figure 8:
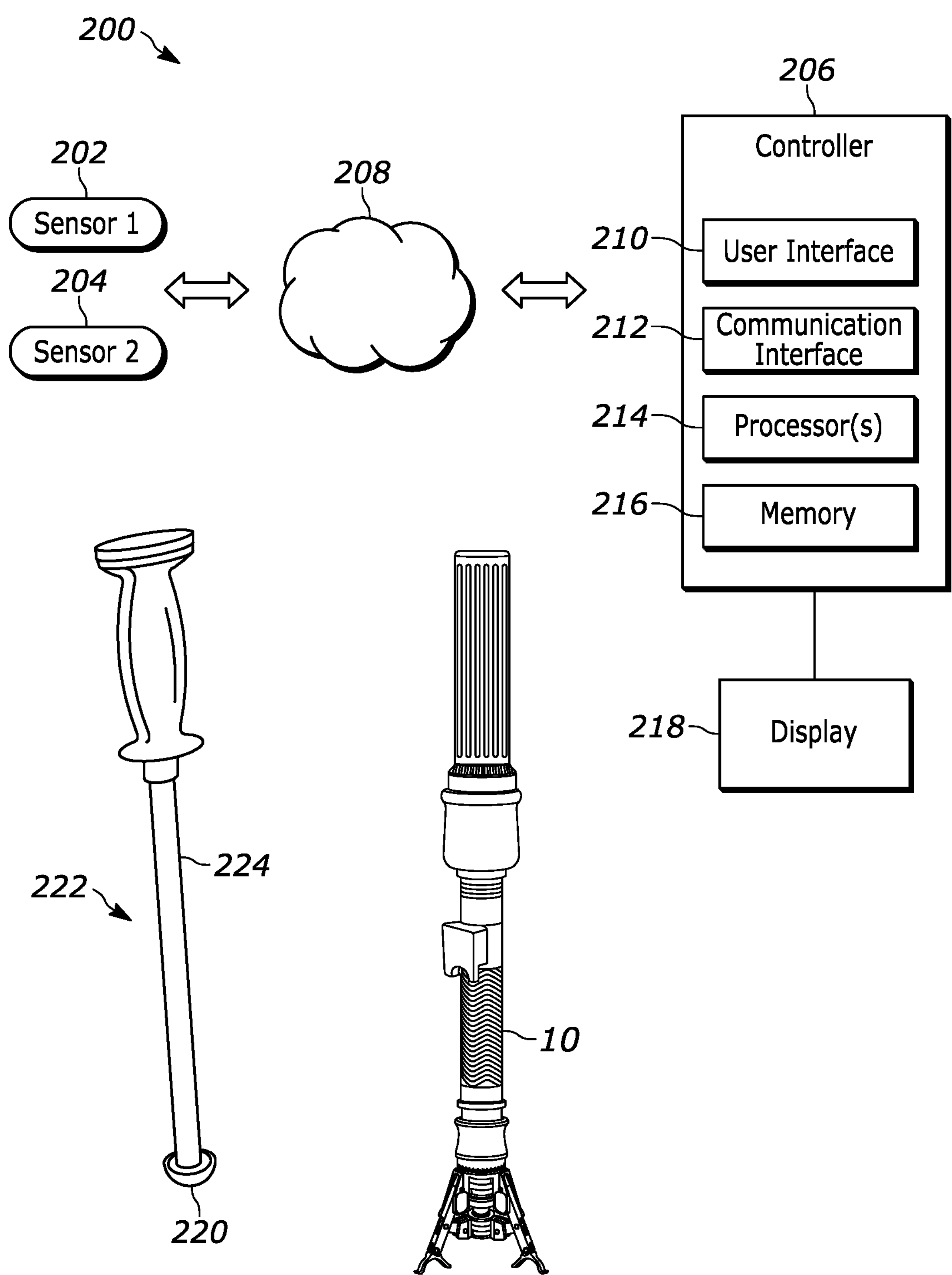
FIG. 8 is a schematic view of an example system for use in performing hip arthroplasty.

As shown in FIG. 8, an example system 200 can include a first position sensor 202 and a second position sensor 204. The first and second position sensors 202, 204 can be configured to communicate position and/or orientation data measured thereby to a controller 206 via a communication network 208. In the implementation shown, the controller 206 can include a user interface 210, a communication interface 212, one or more processors 214, and a memory 216 storing instructions executable by the one or more processors 214 to perform various functions including the disclosed implementations. The user interface 210, the communication interface 212, and the memory 216 are electrically and/or communicatively coupled to the one or more processors 214. The system 200 can further include a display 218 in communication with the controller 206 and configured to display calculated measurements and other data as described herein. As shown and described in more detail below, the system 200 further includes the pelvis registration instrument 10 and an implant 220 to which the first position sensor 202 can be coupled.

In an implementation, the user interface 210 is adapted to receive input from a user and to provide information to the user associated with the operation of the system 200 and/or an analysis taking place. The user interface 210 may include any suitable user input, such as a touch screen, a display, a keyboard, a speaker(s), a mouse, a track ball, and/or a voice recognition system. The touch screen and/or the display may display a graphical user interface (GUI).

In an implementation, the communication interface 212 is adapted to enable communication between the system 200 and a remote system(s) (e.g., the sensors 202, 204, other computers) via the network(s) 208. The network(s) 208 may include, any suitable wired or wireless network, for example, the Internet, an intranet, a local area network (LAN), a wide area network (WAN), a coaxial cable network, a wireless network, a wired network, a satellite network, a digital subscriber line (DSL) network, a cellular network, a Bluetooth connection, a near field communication (NFC) connection, etc.

The one or more processors 214 and/or the system 200 may include one or more of a processor based system(s) or a microprocessor based system(s). In some implementations, the one or more processors 214 and/or the system 200 includes one or more of: a programmable processor, a programmable controller, a microprocessor, a microcontroller, a graphics processing unit (GPU), a digital signal processor (DSP), a reduced instruction set computer (RISC), an application specific integrated circuit (ASIC), a field programmable gate array (FPGA), a field programmable logic device (FPLD), a logic circuit and/or another logic based device executing various functions including the ones described herein.

The memory 216 can include, for example, one or more of: a semiconductor memory, a magnetically readable memory, an optical memory, a hard disk drive (HDD), an optical storage drive, a solid state storage device, a solid state drive (SSD), a flash memory, a read-only memory (ROM), erasable programmable read-only memory (EPROM), electrically erasable programmable read-only memory (EEPROM), a random access memory (RAM), a non-volatile RAM (NVRAM) memory, a compact disc (CD), a compact disc read-only memory (CD-ROM), a digital versatile disk (DVD), a Blu-ray disk, a redundant array of independent disks (RAID) system, a cache, and/or any other storage device or storage disk in which information is stored for any duration (e.g., permanently, temporarily, for extended periods of time, for buffering, for caching).

While the system illustrated in FIG. 8 may be used in connection with a variety of prosthesis implantation procedures, including, for example, knee arthroplasty, shoulder arthroplasty, etc., a more detailed description is provided below with reference to a hip replacement procedure. In such a procedure, the first position sensor 202 can be configured to first couple to the pelvis registration instrument 10 and to subsequently couple to the hip prosthesis 220, e.g., an acetabular cup implant. The second position sensor 204 can be configured to be disposed in a fixed, spaced relation relative to the first position sensor 202. For example, the second position sensor 204 can be coupled to a patient's bony pelvis in order to track movements thereof.

As is explained in more detail below, configuring the radial and circumferential locations of the contact points 20 based on scan data of the patient's anatomy can provide a known reference orientation when the pelvis registration instrument 10 is properly positioned against the patient's anatomy. By capturing position information from the first position sensor 202 when it is coupled to the pelvis registration instrument 10 and when the contact points 20 of the pelvis registration instrument 10 are engaged with the identified locations of the patient's acetabulum 231, and from the second position sensor 204 when it is coupled to the pelvis, calculations can be made by the controller 206 to determine angular relationships, including one or more of: anatomic angle of inclination and anatomic angle of anteversion to guide the placement of the hip prosthesis 220 to a desired angle of inclination and anteversion relative to the patient's pelvis.

After reference data is captured with the pelvis registration instrument 10 in place, the first position sensor 202 can be transferred to a hip prosthesis instrument 222 used to implant the hip prosthesis 220. For example, the instrument 222 can include both the acetabular cup implant 220 and an impactor 224 that is used to implant the implant 220 within a patient's acetabulum 231.

In an alternative example, a single position sensor can be utilized to perform calculations to guide the placement of a hip prosthesis, e.g., an acetabular cup implant, to a desired angle of inclination and anteversion relative to the patient's pelvis. Information can be received from the single electronic position sensor to track movement relative to a reference position established from docking the single position sensor to the pelvis registration instrument 10, then the single position sensor is moved to a fixed reference point on the patient's pelvis. Once the single position sensor has established a frame of reference relative to the patient's pelvis, the single position sensor can be moved from the fixed reference point to one of the prosthesis or instrument to determine the relative alignment of the prosthesis or instrument. This method of operation assumes that a patient's pelvis or other bony anatomy remains stationary during the time that the single position sensor is moved from the pelvis registration instrument 10 to the fixed point on the patient's pelvis and then to one of the prosthesis or instrument, as any movement thereof would not be tracked due to the absence of a second position sensor coupled thereto. Nonetheless, this method of operation can still provide increased accuracy and precision in placing a prosthesis relative to some prior techniques, e.g., those that rely purely on surgeon estimation, etc. Further, by repeatedly transferring the single sensor between a configuration in which it is coupled to the patient's pelvis and a configuration in which it is coupled to an instrument or implant, movement of the pelvis over time can be tracked. For example, movement of the pelvis can be detected by a position change between a first time and a second time that the single sensor was coupled to the pelvis in a same location (e.g., by coupling to one or more pins, as explained herein).

The calculations referenced above can be provided by intra-operative software executed on/by the controller 206. The intra-operative software can be an especially designed and coded program which is operative to read the information sent from the position sensors 202, 204; calculate and display angular relationships, including the angles of inclination and anteversion; and monitor changes in any of these values. These functions and processes can be implemented in software, hardware, firmware, or any combination thereof. The processes can be implemented in one or more computer programs executing on a programmable computer including at least one digital data processor, a storage medium or memory readable by the processor (including, e.g., volatile and non-volatile memory and/or storage elements), user input devices (e.g., the sensors described above, a keyboard, a computer mouse, a joystick, a touchpad, a touchscreen, or a stylus), and one or more output devices (e.g., a computer display). Each computer program can be a set of instructions (program code) in a code module resident in the random access memory of the computer. Until required by the computer, the set of instructions can be stored in another computer memory (e.g., in a hard disk drive, or in a removable memory such as an optical disk, external hard drive, memory card, or flash drive) or stored on another computer system and downloaded via the Internet or other network.

In order to better illustrate the methods and systems of the present disclosure, a description of an exemplary procedure for hip arthroplasty is explained below. While the procedure explained below makes use of the teachings of the present disclosure, it is by no means a limiting example. It will be appreciated that there are many variations on the procedure described below that are within the scope of the disclosure. Further, and as noted above, the teachings of the present disclosure can be applied to any of a variety of procedures where a prosthesis is implanted in a patient's body. These can include, for example, arthroplasty operations in variety of anatomical locations (e.g., knee, hip, shoulder, etc.).

Figure 9:
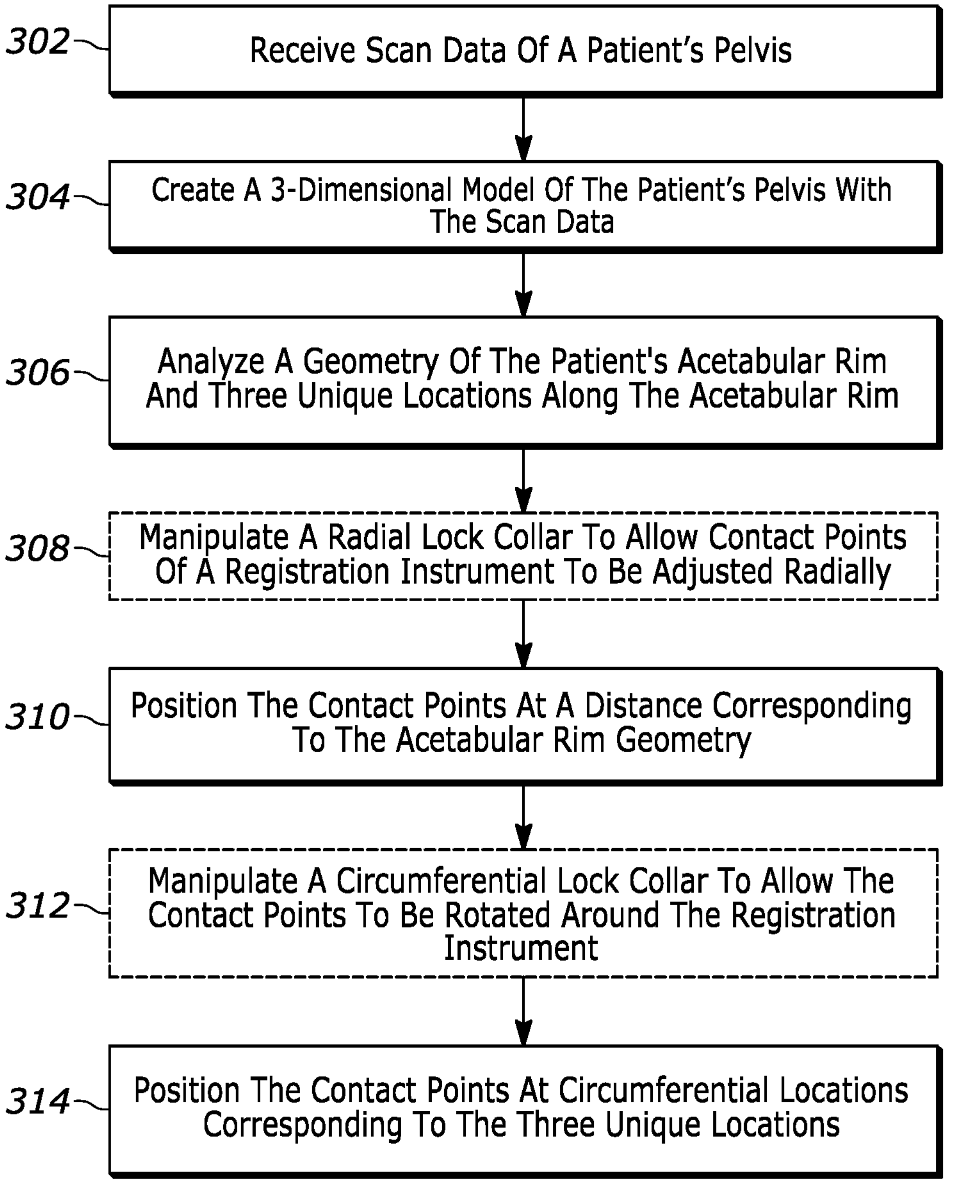
FIG. 9 is a flowchart for an example preparation for a pelvis registration instrument to have a patient-specific configuration.

FIG. 9 illustrates one example of a pre-operative method for configuring the pelvis registration instrument 10 to be a patient-specific pelvis registration guide. The process generally begins by conducting a scan of at least a portion of a patient's anatomy. In the case of hip arthroplasty, such a scan can include a computed tomography (CT) scan of the patient's pelvis 230 and acetabular region. Such a scan can produce, for example, a series of 2-dimensional images taken at different locations along an axis orthogonal to the plane defined by the images. In other embodiments, a magnetic resonance imaging (MRI) scan can be utilized.

Data from such a scan can be transferred to one or more digital data processors that are capable of running image processing software to create a 3-dimensional model of the patient's pelvis from the scan data. Such a transferring process might include a variety of different technologies for relaying data, including, for example, manual transfer of physical media (e.g., a compact disc (CD), flash memory drive, or other portable storage media) or uploading scan data to one or more networked computers or storage devices. Regardless of how the transfer is accomplished, scan data can be made accessible to one or more digital data processors capable of performing the required modeling, as shown by step 302 of FIG. 9. Note that the image processing software can in some examples be executed by the same controller 206 that is used to execute the intra-operative software (e.g., the image processing software and the intra-operative software both be run on the same computing device), while in other example any number of separate computing devices can be utilized.

At step 304, the digital data processor can perform the conversion to create a 3-dimensional model of at least a portion of the patient's anatomy, e.g., a model of the patient's pelvis. As a part of this process, the model can define the anatomical planes of the patient's body based, for example, on the locations of certain anatomical landmarks. For example, for a model of a patient's pelvis, the medial sagittal plane is defined by two points in the middle of a proximal and distal vertebral column and one point on symphysis of the pubis. The image processing software can also create any number of other anatomical planes needed or desired by a user. For example, in some embodiments a surgeon or other user might prefer to reference the anterior pelvis plane that is defined by the left and right ASIS and the left and right pubic tubercles. This plane, and any other plane desired by a user, can be identified and created during the planning process.

At step 306, a user analyzes the model to identify a plurality, such as three or more, unique locations disposed along the patient's acetabular rim 232 and define the anatomic coordinate plane of the acetabular rim 232. Thereafter, at steps 310 and 314, a user can manipulate the pelvis registration instrument 10 to have a patient-specific configuration. For example, at step 310, the user can position the contact points 20 at a radius relative to the centerline of the body 12 corresponding to the specific size of the patient's acetabular rim 232 and, at step 314, a user can position the contact points 20 around the body 12 at circumference locations corresponding to the three unique locations identified in the model. With this configuration, the pelvis registration instrument 10 can be positioned against the patient's acetabular rim 232 in only one orientation. Moreover, because the anatomical—or other user defined—planes of the patient's body have been determined in the 3-dimensional model, a position of the pelvis registration instrument 10 relative to any or all of these planes can be determined when the pelvis registration instrument 10 is interfaced with the patient's acetabular rim 232. That is, the pelvis registration instrument 10 can provide a known reference position/orientation when interfaced with the patient's acetabular rim 232.

In one example, step 310 can include rotating the handle 56 of the pelvis registration instrument 10 to move the inner shaft 50 of the body 12 along the longitudinal axis L of the body 12 relative to the outer shaft 48 of the body 12. As discussed above, with this configuration, movement of the inner shaft 50 causes the leg members 28 of the engagement assembly 18 to pivot about pivot axes P1 perpendicular to the longitudinal axis L of the body 11. In one example, step 314 can include moving the leg linkages 26 around a perimeter of the body 12.

In further examples, the method can include, at step 308, manipulating a radial lock collar 66 arranged around the body 12 to disengage the radial lock collar 66 from the handle 56, which allows the handle 56 to be rotated relative to the outer shaft 48 and/or, at step 312, manipulating a circumferential lock collar 102, 102' arranged around the body 12 to disengage the circumferential lock collar 102, 102' from the leg linkages 26, which allows the leg linkages 26 to be moved around the perimeter of the body 12.

FIGS. 10-14 illustrate one embodiment of a surgical procedure according to the teachings of the present disclosure. Such a procedure is typically performed after a surgeon or other user has analyzed the model and configured the pelvis registration instrument 10 as described above with respect to FIG. 9 for use in the operation. The procedure can begin with a surgeon preparing a patient's pelvis or other bony anatomic structure 230 to receive the second position sensor 204. Positioning the second position sensor 204 can utilize one, two or more surgical pins 234, 236 to fix the position sensor 204 relative to the bony anatomic structure 230 of the patient. For example, first and second surgical pins 234, 236 can be driven into the pelvis 230 of a patient. Any suitable location can be utilized depending on approach and preference. The second position sensor 204 need only serve as a fixed reference on the patient's pelvis or other bony anatomic structure and need not also be a direct reference to an anatomical plane or axis of the patient's body. This significantly eases use of the system, reduces complexity for a surgeon or other user, and eliminates potential sources of error in the accuracy of the procedure. The pin(s) and other mounting structure can engage the second position sensor 204 to restrict relative movement thereof. For example, the pin(s) 234, 236 can extend through portions of the sensor 204, the mounting structure can releasably couple to the sensor 204 by any suitable mechanism, such as snap-fit, tongue-and-groove, latching, and so forth.

In one example, the system 200 can continuously monitor the patient's pelvis position to continuously calculate the angular relationships described above and, as a consequence of this capability, the surgeon can effectively ensure an accurate angular placement of the acetabular prosthesis within the host's native bone without compromising stability of the reconstructed joint. In another example, the system 200 can be configured to monitor the patient's pelvis position and calculate the angular relationships on demand.

In some embodiments, the second position sensor 204 can be a micro-electromechanical system (MEMS) multi-axis position sensor that is calibrated in all three X, Y, and Z Axes. The second position sensor 204 can be coupled to the bony pelvis 230 (or other bony anatomic structure in the case of operations on knees, wrists, shoulders, or other parts of the body) at any desired location, as described above, using, e.g., securing pins 234, 236. The first position sensor 202 can be an electronic position and rotation sensor much like the second position sensor 204, and it can also be calibrated to make digital measurements in all three X, Y, and Z Axes. The first sensor 202 can measure angles for determining the position of the acetabular prosthetic implant as a single electronic calculation. Angles of inclination and anteversion can be calculated by the intra-operative software when the second sensor 204 is used in combination with the first sensor 202. The first and second sensors 202, 204 can communicate through a wired connection or wirelessly with the controller 206 and/or with one another.

As described below via the exemplary hip joint prosthetic surgery, the first sensor 202 can be primarily focused upon determining the position of the pelvis registration instrument 10 and the acetabular prosthesis 220 when each one is being implanted in situ. To achieve this, the first sensor 204 can be typically coupled to the pelvis registration instrument 10 or the cup impactor or other insertion instrument 222 in order to show the position and placement orientation for the implanted prosthesis 220 at that moment in time. Accordingly, the first sensor 202 can measure the angles for both of two different parameters: (i) the anatomic angles then existing for the host's acetabulum 231; and (ii) the position angles of the acetabular prosthesis 220 then being implanted by the surgeon.

In one example, the position sensors 202, 204 can have at least one orientation sensor and at least one transmitter, or wireless antenna. The transmitter can be any of a variety of types used to transmit information, including wirelessly, over the network 208. In other examples, the sensors 202, 204 can be wired together. The orientation sensors can preferably specify the tilt of the sensor with respect to orthogonal axes (such as x-y-z axes) and heading with respect to an external field. The external field measured by the first and second electronic position sensors 202, 204 can be the Earth's magnetic field, for example.

By way of further example, a position sensor described herein can include the following components: a tilt sensor module and a direction sensor module built in a MEMS (micro electro mechanical system) chip; a wireless communication module; a micro controller unit to operate the systems; an internal power source; and a printed circuit board onto which the other components can be placed. The microcontroller unit can manage all of functions and performance of the main electronic components of the sensor. The power source can be any suitable batteries or other power source that can provide sufficient power to the sensor.

In some examples, the tilt sensor can be an accelerometer capable of measuring degrees of tilt from the true horizontal plane in three different axes. It can be used for sensing position and degree of tilt of a patient's pelvis from a vertical position. It can also be used for sensing a degree of tilt of an implant from a horizontal plane.

In some examples, the direction sensor can be a digital magnetometer capable of showing the direction of the axis of an object. The sensor can be used to sense the direction of the pelvis. An additional sensor can sense the implant vector of the acetabular cup when attached to an instrument that is used for placement of the cup.

In some examples, an exemplary device can include a 3D digital linear acceleration sensor, a 3D digital gyroscope, and a 3D digital magnetic sensor. If desired, operation can be conducted without use of a magnetic sensor to avoid interference from metal objects in an operating room, etc. The output from such a system can be converted in software, firmware, or the like into the tilt data utilized by the systems and methods described herein.

In some embodiments, a communication module can be included in a position sensor and utilized to provide a wireless mode of communication between the sensor and the controller 206. It can wirelessly transfer raw data from the sensor 202, 204 so that the controller 206 can receive the data and calculate the position angles of the pelvis 230 and implant 220. A graphical user interface 218, 210 can be provided to show the data to a user.

Figure 10:
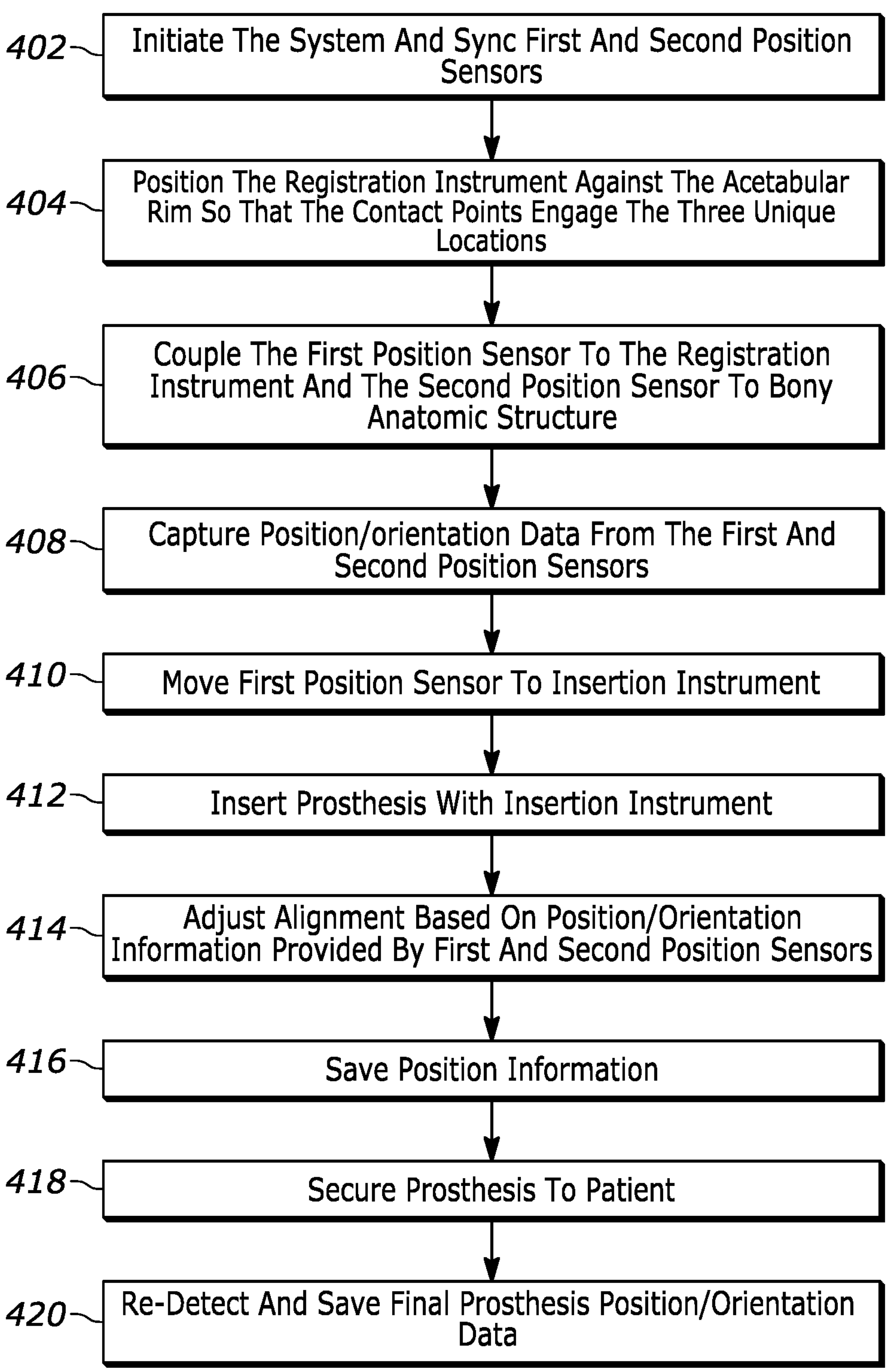
FIG. 10 is a flowchart for an example hip arthroplasty procedure using a pelvis registration instrument.

Having prepared the patient's pelvis or other bony anatomic structure 230 to receive one or more electronic position sensors, a surgeon or other user can proceed using the method shown in FIG. 10. The first step in such a procedure can be to initiate the system and sync the first and second position sensors 202, 204, as shown at step 402. An initial interface presented to the surgeon or other user can prompt the user for entry of identifying information for the patient and/or pelvis registration instrument 10. This can include, for example, entering a patient identification code, entering a code printed on the pelvis registration instrument 10, scanning a barcode or other indicia accompanying the pelvis registration instrument 10, etc. Upon entry of such identifying information, the intra-operative software can load information, such as the angles of inclination and forward flexion of the pelvis registration instrument 10 when in position against a patient's anatomy, into memory. In some embodiments, this information can be entered manually (e.g., in an example where such information is printed directly on the pelvis registration instrument 10 or the physician can analyze the model rather than a patient identifying or other code), while in other example this information can be downloaded from a digital data repository via a network connection using, for example, the patient identifying code to access the correct information.

The intra-operative software can also prompt a user to enter desired angles of inclination and anteversion. Entry of such information can allow the intra-operative software to perform calculations and provide guidance toward a desired position while saving a surgeon or other user from performing calculations in their head based on the angles provided by the pelvis registration instrument 10.

In addition to initiating the intra-operative software, syncing of the first and second position sensors 202, 204 can increase their precision, as any differences in measurement can be offset. By way of further explanation, inertial sensors of the type utilized in the first and second position sensors 202, 204 can be subject to variation from one another (e.g., when oriented in the same direction, each sensor can report small differences in its orientation) and this variation can change over time. Syncing the sensors can eliminate any inherent variation and can reset any drift error to zero at the commencement of a procedure. Syncing the first and second position sensors 202, 204 to one another can be done in a variety of manners. For example, in some embodiments the system 200 can include a stacking tray (not shown) or other fixture to align the two sensors 202, 204 in the same orientation. Alternatively, the sensors 202, 204 can be stacked on top of one another over the pins 234, 236 that are already implanted in the patient's pelvis or other bony anatomic structure 230.

At step 404, a user positions the pelvis registration instrument 10 against the acetabular rim 232 of the patient, such that the three contact points 20, e.g., feet 22, engage the three unique circumferential points previously identified along the circumference of the acetabular rim 232. Either before or after positioning the pelvis registration instrument 10 against the acetabular rim 232 of the patient, at step 406 the user can couple the first position sensor 202 to the pelvis registration instrument 10, such as to the sensor mount 112 thereof, and can couple the second position sensor 204 to the bony anatomic structure 230 of the patient.

Figure 11:
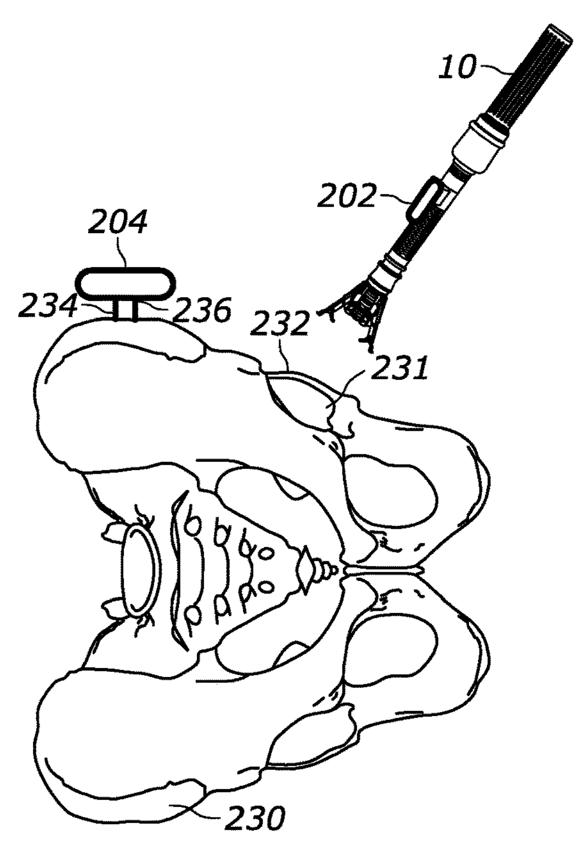
FIG. 11 is a schematic view of a first example step for a hip arthroplasty procedure utilizing a pelvis registration instrument with first and second position sensors.
Figure 12:
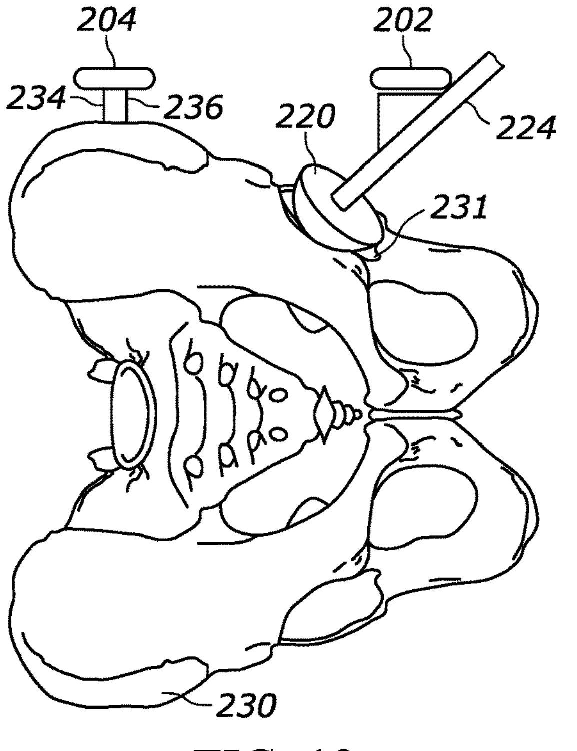
FIG. 12 is a schematic view of a second example step for a hip arthroplasty procedure utilizing a hip prosthesis instrument with the first and second position sensors of FIG. 11.

Regardless of how the motion capture is initiated or otherwise implemented, the processor can receive position and orientation data from the first and second position sensors 202, 204 when in the configuration shown in FIG. 11, as shown in step 408 of FIG. 10. This can serve as a reference position that can be returned to after the pelvis registration instrument 10 is removed and an acetabular implant 220 is inserted in its place. Moreover, because the relative angles between the pelvis registration instrument 10 and the anatomical planes of the patient's body are known when the pelvis registration instrument 10 is in position, the reference positions of the first and second sensors 202, 204 can be related to angles relative to the anatomical planes/axes of the patient's body through calculations performed by the controller 206. This can allow the controller 206 to guide a surgeon or other user, via, for example, data shown on the display/interface 218, 210, to an implant orientation having a desired angle of inclination and/or anteversion.

At step 410 of FIG. 10, the first position sensor 204 is removed from the pelvis registration instrument 10 and coupled to the impactor 224 such that the first position sensor 202 can transmit data on a position of the impactor 224 and the implant 220 coupled thereto. This process includes removing the pelvis registration instrument 10 and any necessary preparation for the implant 220, e.g., reaming, etc., can be performed. An impactor 224 or other insertion instrument can be coupled to an acetabular cup implant 220 or other prosthesis and readied for insertion into the acetabulum 231.

At step 412 of FIG. 10, the prosthesis 220 can be inserted into the acetabulum 231 of the patient's pelvis 230 using the impactor 224. The first and second position sensors 202, 204 can transmit position and orientation data to the controller 206, which can then calculate the current, real-time position and/or orientation of the patient's pelvis 230 or the prosthesis/impactor 220, 224, e.g., the angular relationships of the prosthesis relative to the pelvis 230, as well as provide real-time updates to a surgeon or other user on any changes in position and orientation thereof. Using calculations performed by the controller 206, such position and/or orientation information can be displayed in relation to the bony anatomic structure 230 (i.e., the pelvis) or any desired planes, including, for example, the sagittal, coronal, or transverse planes, as well as any other planes desired by a user, such as the anterior pelvis plane discussed above.

In the next illustrated step of FIG. 10, step 414, the controller 206 provides guidance to a user to move the instrument 222 with the first position sensor 204 coupled thereto. This can include providing guidance such that the position and orientation data from the first and second position sensors 202, 204 matches the data provided with the first sensor 202 coupled to the pelvis registration instrument 10, for example, or is offset a predetermined amount. A surgeon or other user can then adjust alignment of the prosthesis 220 based on feedback provided by the display/interface 218, 210 to arrive at a desired angle of inclination and/or angle of anteversion for the prosthesis.

Figure 13:
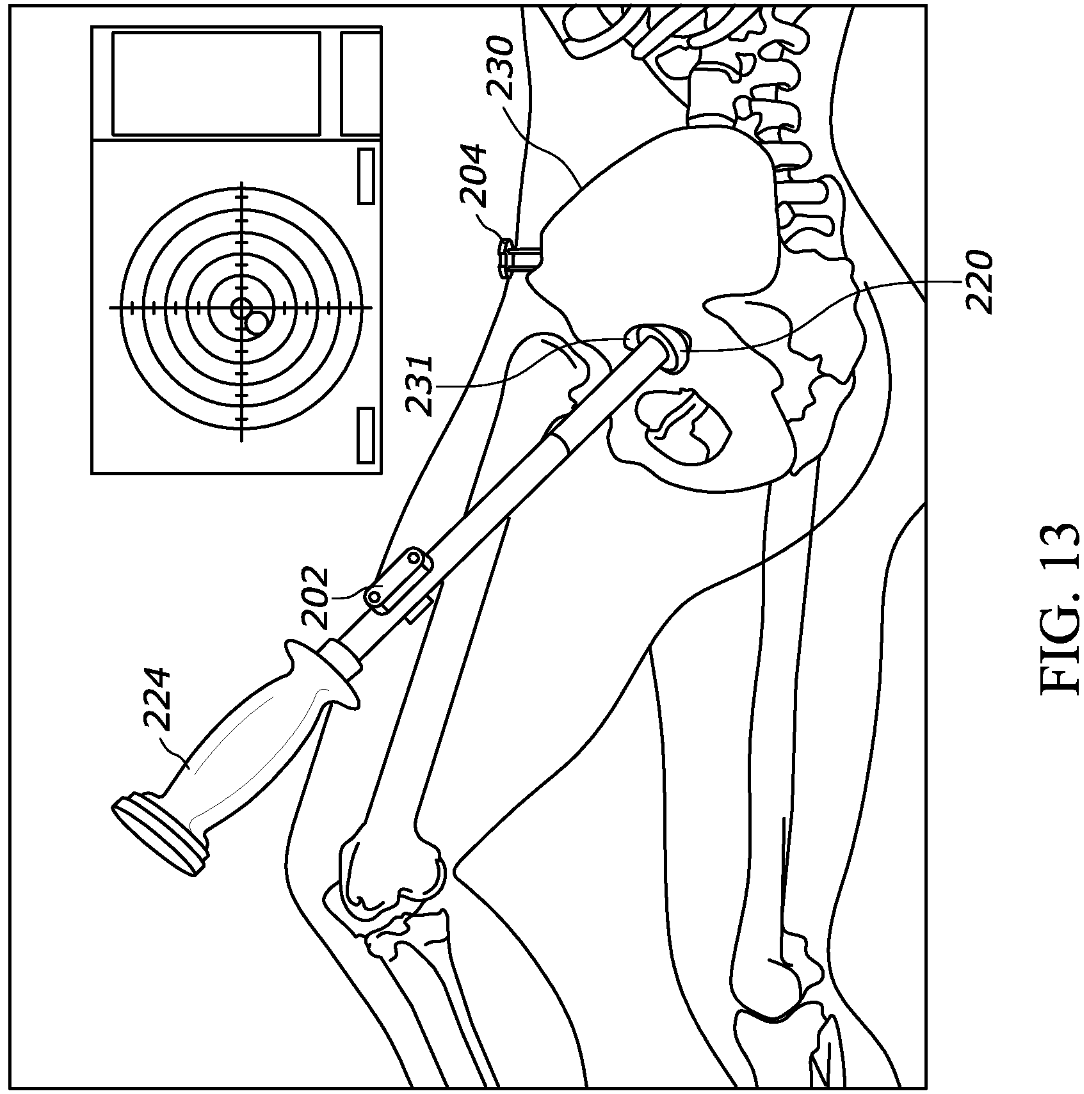
FIG. 13 is a schematic view of an example display for guiding positioning of a hip prosthesis using first and second position sensors.
Figure 14:
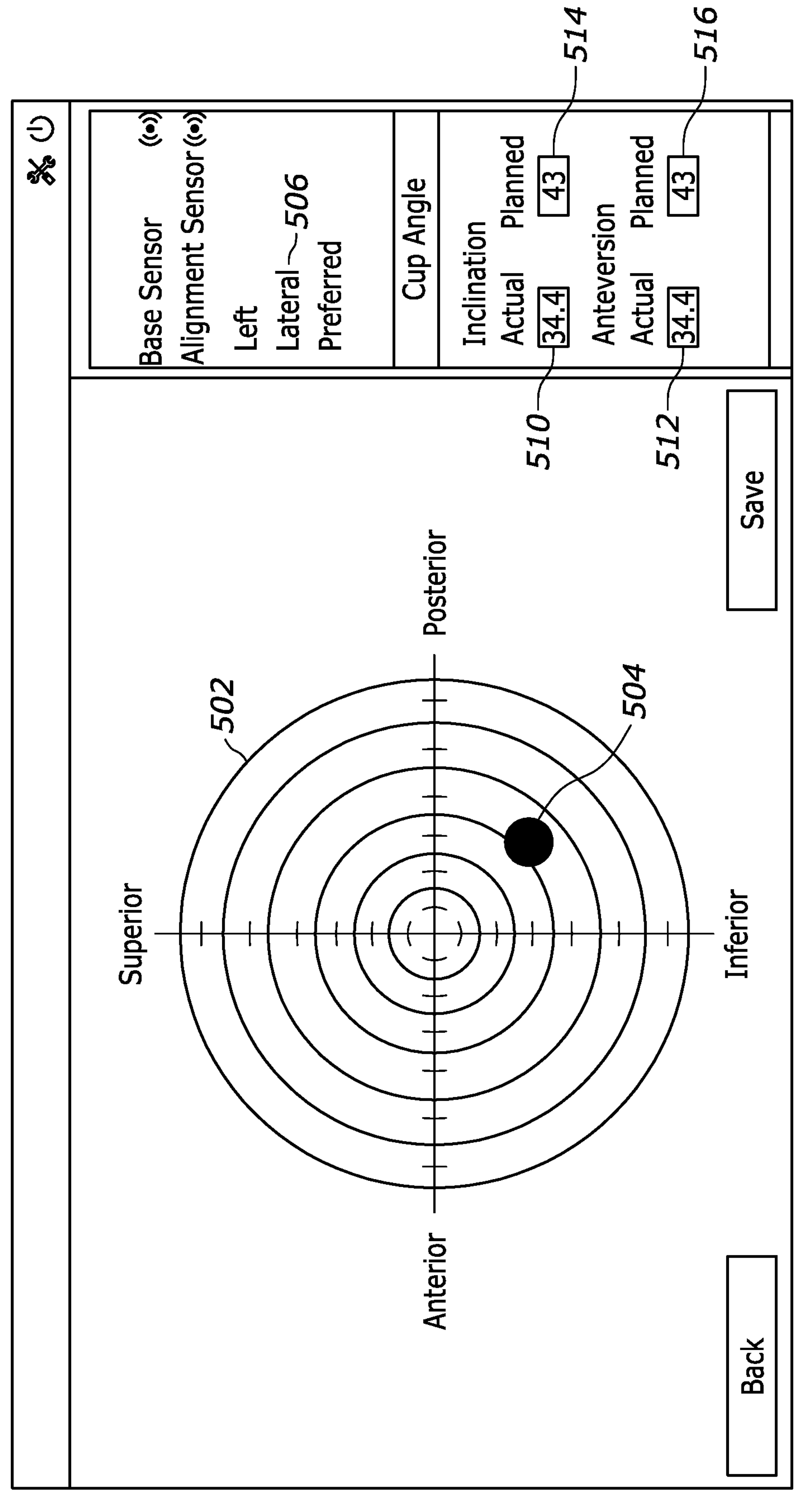
FIG. 14 is a schematic view of a portion of the display of FIG. 13 in greater detail.

FIGS. 13 and 14 illustrate one embodiment of this process in more detail, where an exemplary display 500 is shown with a "target" graphic to help guide a surgeon or other user in positioning the acetabular cup implant 220 into a desired position using the impactor 224. The graphic, including current and desired angular measurements along a right side thereof in some embodiments, can be calculated and updated in real time by the controller 206 based on data received from the first position sensor 202 that is coupled to the patient's pelvis and the first position sensor 202 that is coupled to the impactor 224. Although the first sensor 202 is shown in FIG. 13 coupled to the impactor 224 in an orientation parallel to a longitudinal axis thereof, other suitable orientations can be utilized.

With reference to the detail view of display 500 shown in FIG. 14, the "target" guidance graphic 502 can be centrally located to provide easily ascertainable visual guidance to a surgeon or other user regarding positioning of the prosthesis 220. The graphic can include color coding in some embodiments, such that the positioning dot 504 symbolizing the position/orientation of the prosthesis can be colored, e.g., green if within 5° (or less) of desired or planned angle, yellow if within 5-10°, and red if farther than 10° from the desired or planned angle.

On the right hand side of the display 500 an be indications 506 of surgical approach and operative side (e.g., right or left hip, etc.) or other identifying information, such as a patient ID, alignment instrument ID, prosthesis ID, etc. Further information can also be included along a bottom portion of the display 500. The display can also include a portion showing numeric prosthesis position and orientation information. Example measures can include the angle of inclination 510 and the angle of anteversion 512, as well planned angles of inclination 514 and anteversion 516. The latter angles can be adjustable by a user via an interface (e.g., a touchscreen of a tablet device, etc.).

Once a desired position and orientation has been achieved, a surgeon or other user can fix the implant in place using a conventional method. As noted in step 416 of FIG. 10, after fixation a surgeon can elect to save the final positioning information of the prosthesis 220. In some embodiments, however, additional fixation elements, such as screws, cement, or other methods known in the art can be utilized to secure the prosthesis 220 to the patient, as shown by step 418 in FIG. 10. Typically, the impactor 224 or other insertion instrument is removed from the prosthesis 220 to facilitate application of any fixation method. Such installation can cause movement of the implant 220 in some cases, so a surgeon or other user might also elect to reattach the impactor 224 or other insertion instrument after installing any screws or other fixation elements to measure and save an ultimate final position and/or orientation of the prosthesis, as shown in step 420 of FIG. 10.

The terms "substantially," "approximately," and "about" where used throughout this specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A pelvis registration apparatus comprising:

a body having a distal end and a proximal end, the body extending along a longitudinal axis; and an engagement assembly coupled to the distal end of the body and comprising three or more contact points, wherein the contact points are:

selectively movable radially with respect to the longitudinal axis to position the contact points at a desired distance relative to a centerline of the body; and selectively movable about the body to position the contact points at desired circumferential locations relative to one another:

wherein:

the engagement assembly comprises a plurality of leg linkages coupled to the body, each leg linkage providing one or more of the contact points, the leg linkages each comprising a leg member having a proximal end and an opposite, distal end;

the proximal ends of the leg members are pivotably coupled to the body about a pivot axis perpendicular to the longitudinal axis to position the distal ends of the leg members at the desired distance;

the leg linkages are rotatable about the body to selectively position the leg assemblies at desired circumferential locations;

each leg linkage further comprises a support member having a proximal end pivotably coupled to the body and a distal end pivotably coupled to an intermediate portion of the leg member; and the body comprises an outer shaft and an inner shaft extending within the outer shaft, the proximal ends of the support member are coupled to the inner shaft; and further comprising a handle coupled to the inner shaft and threadingly engaged with the outer shaft, such that rotation of the handle causes the inner shaft to move longitudinally with respect to the outer shaft, movement of the inner shaft causing the support member to move the distal ends of the leg members radially with respect to the body.

2. The pelvis registration apparatus of claim 1, further comprising one or more locking mechanisms to restrict movement of the contact points relative to the body.

3. The pelvis registration apparatus of claim 1, wherein, for each leg linkage, the contact point is a foot pivotably coupled to the distal end of the leg member.

4. The pelvis registration apparatus of claim 1, wherein one of the outer shaft or handle includes sizing gradation indications thereon; and the other of the outer shaft or handle includes a line movable with respect to the sizing gradation indications to indicate sizing distances on which the feet of the leg linkages are disposed.

5. The pelvis registration apparatus of claim 1, further comprising a radial lock collar arranged around the body, the radial lock collar slidable with respect to the handle along the longitudinal axis and biased to a locked position preventing rotation of the handle relative to the outer shaft.

6. The pelvis registration apparatus of claim 1, wherein each leg linkage further comprises:

a top mount including a bracket having the proximal end of the leg member pivotably mounted thereto and a guide disc extending radially inward from the bracket, the guide disc arranged around the body and fixed with respect to the outer shaft; and a bottom mount including a bracket having the proximal end of the support member pivotably mounted thereto and a follower disc extending radially inward from the bracket, the follower disc extending around the body and fixed with respect to the outer shaft.

7. The pelvis registration apparatus of claim 6, wherein the guide discs and the follower discs of the leg linkages are disposed in a stacked relation to one another along the body.

8. The pelvis registration apparatus of claim 6, wherein the bracket of the top mount includes one or more grip recesses for aiding in circumferential leg assembly adjustment.

9. The pelvis registration apparatus of claim 6, wherein the outer shaft comprises an extension tip extending distally therefrom around the inner shaft, the guide discs of the leg assemblies being disposed around the extension tip.

10. The pelvis registration apparatus of claim 9, further comprising a slider mounted to the extension tip distally of the guide discs, the slider configured to engage the brackets of the top mounts to prevent unwanted circumferential movement thereof.

11. The pelvis registration apparatus of claim 9, further comprising a circumferential lock collar arranged around the extension tip and longitudinally movable with respect thereto, the circumferential lock collar slidable with respect to the extension tip along the longitudinal axis and biased to a locked position engaging the top mounts of the leg assemblies and preventing circumferential movement of the leg assemblies relative to the extension tip.

12. The pelvis registration apparatus of claim 11, wherein the extension tip further comprises an outwardly extending ring portion, the ring portion configured to provide a stop surface for the circumferential lock collar when manipulated away from the locked position to allow circumferential movement of the leg assemblies.

13. The pelvis registration apparatus of claim 11, wherein the extension tip includes angular gradation indications therearound; and each top mount of the leg assemblies includes a pointer or protrusion shiftable along the angular gradation indications when the leg assemblies are manipulated around the body to indicate a circumferential location for each of the contact points.

14. The pelvis registration apparatus of claim 1, further comprising a sensor mount coupled to the body, the sensor mount configured to have a sensor removably coupled thereto.

15. The pelvis registration apparatus of claim 1, wherein at least one of the body or engagement assembly includes openings extending therethrough to provide access to interior surfaces thereof for cleaning.

16. A pelvis registration apparatus comprising:

a body having a distal end and a proximal end, the body extending along a longitudinal axis;

an engagement assembly coupled to the distal end of the body and comprising three or more contact points, wherein the contact points are:

selectively movable radially with respect to the longitudinal axis to position the contact points at a desired distance relative to a centerline of the body; and selectively movable about the body to position the contact points at desired circumferential locations relative to one another; and acetabulum data from one or more computed tomography scans of a patient, the desired distances relative to the centerline of the body and the desired circumferential locations for the contact points of the engagement assembly being determined based on the acetabulum data.

17. A system for use in implanting a prosthesis, the system comprising:

a pelvis registration apparatus comprising:

a body having a distal end and a proximal end, the body extending along a longitudinal axis; and an engagement assembly coupled to the distal end of the body and comprising three or more contact points, wherein the contact points are:

selectively movable radially with respect to the longitudinal axis to position the contact points at a desired distance relative to a centerline of the body; and selectively movable about the body to position the contact points at desired circumferential locations relative to one another;

a controller; and first and second position sensors capable of reporting position and orientation data to the controller, the first position sensor being removably coupled to the pelvis registration apparatus and the second position sensor disposed in a fixed, spaced relation relative to the first position sensor, wherein the second position sensor is configured to be coupled to a patient's bony anatomic structure;

wherein the controller is configured to:

receive the position and orientation data from the first and second position sensors; and calculate angular relationships derived from the position and orientation data.

18. The system of claim 17, wherein the bony anatomic structure is the pelvis.

19. The system of claim 17, wherein the angular relationships include one or more of angle of inclination or angle of anteversion.

20. The system of claim 17, wherein the controller is configured to calculate the angular relationships on demand.

21. The system of claim 17, wherein the controller is configured to calculate the angular relationships continuously in real time.

* * * * *